(12) United States Patent
Koblish et al.

(10) Patent No.: US 7,186,250 B2
(45) Date of Patent: *Mar. 6, 2007

(54) METHOD AND APPARATUS FOR POSITIONING A DIAGNOSTIC OR THERAPEUTIC ELEMENT WITHIN THE BODY AND TIP ELECTRODE FOR USE WITH SAME

(75) Inventors: Josef V. Koblish, Palo Alto, CA (US); David K. Swanson, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 210 days.

This patent is subject to a terminal disclaimer.

(21) Appl. No.: 10/658,616

(22) Filed: Sep. 8, 2003

(65) Prior Publication Data

US 2004/0049182 A1 Mar. 11, 2004

Related U.S. Application Data

(63) Continuation of application No. 09/534,713, filed on Mar. 24, 2000, now Pat. No. 6,645,200, which is a continuation-in-part of application No. 09/072,872, filed on May 5, 1998, now Pat. No. 6,142,994, which is a continuation-in-part of application No. 08/949,117, filed on Oct. 10, 1997, now Pat. No. 6,152,920.

(51) Int. Cl.
*A61B 18/18* (2006.01)
(52) U.S. Cl. .................................................. 606/41
(58) Field of Classification Search ............... 128/898; 606/27–52
See application file for complete search history.

(56) References Cited

U.S. PATENT DOCUMENTS

| 463,785 | A | 11/1891 | Connable |
| 4,011,872 | A | 3/1977 | Komiya |
| 4,181,131 | A | 1/1980 | Ogiu |
| 4,493,320 | A | 1/1985 | Treat |
| 4,517,975 | A | 5/1985 | Garito et al. |
| 4,532,924 | A | 8/1985 | Auth et al. |
| 4,565,200 | A | 1/1986 | Cosman |
| 4,651,734 | A | 3/1987 | Doss et al. |
| 4,681,122 | A | 7/1987 | Winters et al. |
| 4,765,331 | A | 8/1988 | Petruzzi et al. |
| 4,800,899 | A | 1/1989 | Elliott |
| 4,920,978 | A | 5/1990 | Colvin |
| 5,013,312 | A | 5/1991 | Parins et al. |
| 5,078,716 | A | 1/1992 | Doll |

(Continued)

FOREIGN PATENT DOCUMENTS

EP 0453071 A1 10/1991

(Continued)

OTHER PUBLICATIONS

US 5,688,268, 11/1997, Billings (withdrawn)

*Primary Examiner*—Michael Peffley
*Assistant Examiner*—Pete Vrettakos
(74) *Attorney, Agent, or Firm*—Henricks, Slavin & Holmes LLP

(57) ABSTRACT

Surgical methods and apparatus for positioning diagnostic an therapeutic elements on the epicardium or other organ surface. The apparatus include a relatively short shaft and an adjustable loop structure that supports

11 Claims, 16 Drawing Sheets

U.S. PATENT DOCUMENTS

| | | |
|---|---|---|
| 5,088,997 A | 2/1992 | Delahuerga et al. |
| 5,092,314 A | 3/1992 | Zeitels |
| 5,108,391 A | 4/1992 | Flachenecker et al. |
| 5,122,137 A | 6/1992 | Lennox |
| 5,131,379 A | 7/1992 | Sewell, Jr. |
| 5,147,357 A | 9/1992 | Rose et al. |
| 5,244,462 A | 9/1993 | Delahuerga et al. |
| 5,249,121 A | 9/1993 | Baum et al. |
| 5,277,201 A | 1/1994 | Stern |
| 5,318,564 A | 6/1994 | Eggers |
| 5,324,288 A | 6/1994 | Billings et al. |
| 5,342,356 A | 8/1994 | Ellman et al. |
| 5,370,650 A | 12/1994 | Tovey et al. |
| 5,381,896 A | 1/1995 | Simons |
| 5,383,876 A | 1/1995 | Nardella |
| 5,401,274 A | 3/1995 | Kusunoki |
| 5,403,342 A | 4/1995 | Tovey et al. |
| 5,415,656 A | 5/1995 | Tihon et al. |
| 5,437,664 A | 8/1995 | Cohen et al. |
| 5,437,665 A | 8/1995 | Munro |
| 5,451,224 A | 9/1995 | Goble et al. |
| 5,486,173 A | 1/1996 | Vancaillie |
| 5,505,730 A | 4/1996 | Edwards |
| 5,562,720 A | 10/1996 | Stern et al. |
| 5,569,242 A | 10/1996 | Lax et al. |
| 5,571,098 A | 11/1996 | Domankevitz et al. |
| 5,626,607 A | 5/1997 | Malecki et al. |
| 5,630,426 A | 5/1997 | Eggers et al. |
| 5,658,280 A | 8/1997 | Issa |
| 5,676,678 A | 10/1997 | Schad |
| 5,681,282 A | 10/1997 | Eggers et al. |
| 5,683,366 A | 11/1997 | Eggers et al. |
| 5,688,266 A | 11/1997 | Edwards et al. |
| 5,697,536 A | 12/1997 | Eggers et al. |
| 5,697,882 A | 12/1997 | Eggers et al. |
| 5,697,909 A | 12/1997 | Eggers et al. |
| 5,702,438 A | 12/1997 | Avitall |
| 5,720,745 A | 2/1998 | Farin et al. |
| 5,730,124 A * | 3/1998 | Yamauchi |
| 5,730,704 A | 3/1998 | Avitall |
| 5,733,280 A | 3/1998 | Avitall |
| 5,738,683 A | 4/1998 | Osypka |
| 5,779,722 A | 7/1998 | Shturman et al. |
| 5,788,688 A | 8/1998 | Bauer et al. |
| 5,823,956 A | 10/1998 | Roth et al. |
| 5,833,690 A | 11/1998 | Yates et al. |
| 5,836,947 A | 11/1998 | Fleischman et al. |
| 5,868,742 A | 2/1999 | Manes et al. |
| 5,871,523 A | 2/1999 | Fleischman et al. |
| 5,895,386 A | 4/1999 | Odell et al. |
| 5,908,420 A | 6/1999 | Parins et al. |
| 5,910,129 A | 6/1999 | Koblish |
| 5,947,964 A | 9/1999 | Eggers et al. |
| 6,012,457 A | 1/2000 | Lesh |
| 6,071,281 A | 6/2000 | Burnside |
| 6,076,012 A | 6/2000 | Swanson et al. |
| 6,120,496 A | 9/2000 | Whayne |
| 6,139,538 A | 10/2000 | Houghton |
| 6,142,994 A | 11/2000 | Swanson et al. |
| 6,152,920 A | 11/2000 | Thompson et al. |
| 6,161,543 A | 12/2000 | Cox et al. |
| 6,171,275 B1 | 1/2001 | Webster |
| 6,190,382 B1 | 2/2001 | Ormsby |
| 6,203,525 B1 | 3/2001 | Whayne |
| 6,237,605 B1 | 5/2001 | Vaska et al. |
| 6,267,760 B1 | 7/2001 | Swanson |
| 6,283,935 B1 | 9/2001 | Laufer et al. |
| 6,290,699 B1 | 9/2001 | Hall et al. |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,416,505 B1 | 7/2002 | Fleischman et al. |
| 6,425,895 B1 | 7/2002 | Swanson et al. |
| 6,468,272 B1 | 10/2002 | Koblish et al. |
| 6,645,200 B1 | 11/2003 | Koblish et al. |
| 6,679,269 B2 * | 1/2004 | Swanson .................... 128/898 |
| 2004/0267106 A1 * | 12/2004 | Segner et al. ............... 600/374 |

FOREIGN PATENT DOCUMENTS

| | | |
|---|---|---|
| EP | 0797956 A2 | 10/1997 |
| WO | WO 93/08755 A1 | 5/1993 |
| WO | WO 96/37156 A1 | 11/1996 |
| WO | WO 97/17027 A1 | 5/1997 |
| WO | WO 97/30644 A1 | 8/1997 |
| WO | WO 97/41793 A1 | 11/1997 |
| WO | WO 98/17187 A1 | 4/1998 |
| WO | WO 98/26724 A1 | 6/1998 |
| WO | WO 99/04696 A1 | 2/1999 |
| WO | WO 99/18878 A2 | 4/1999 |

* cited by examiner

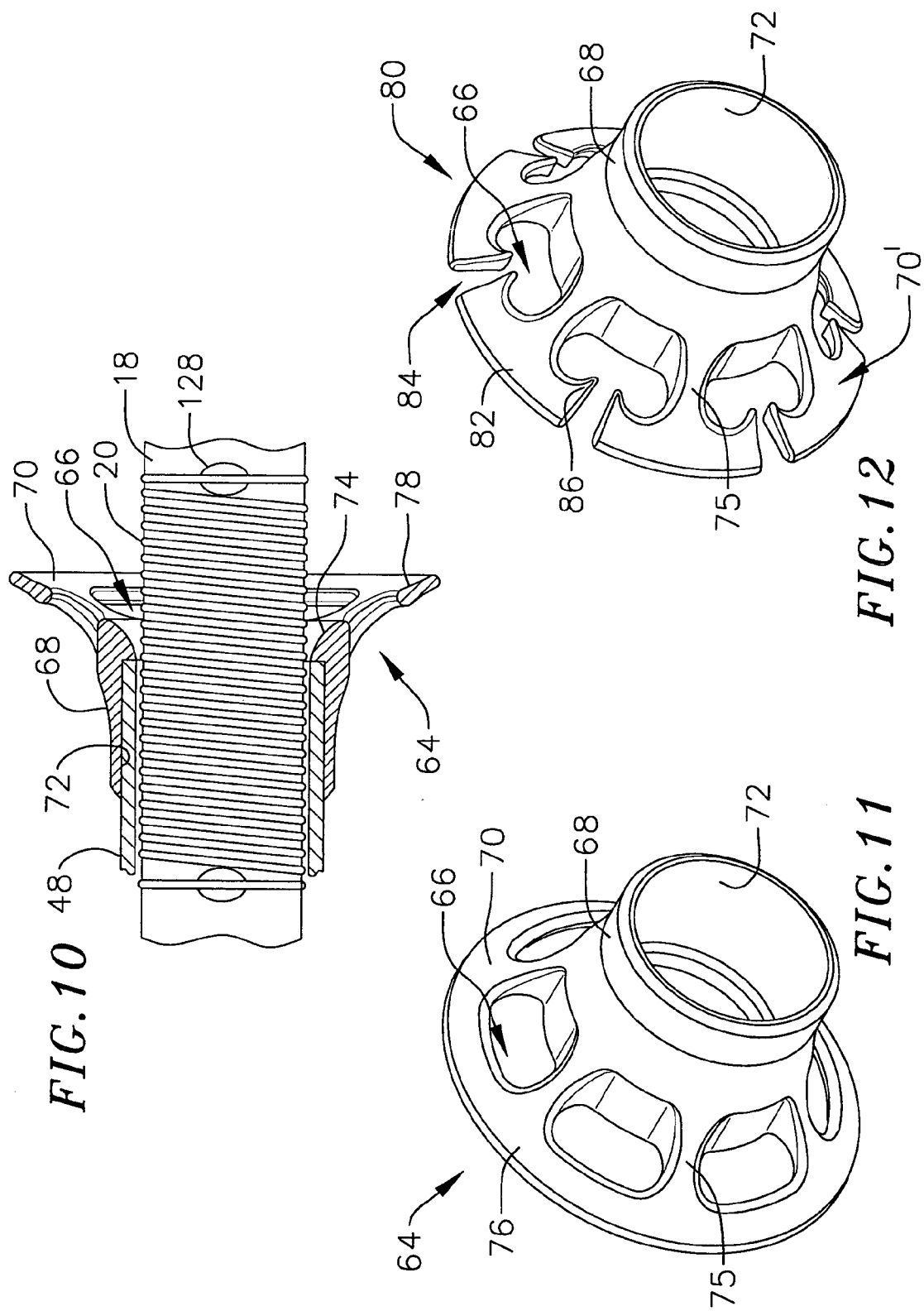

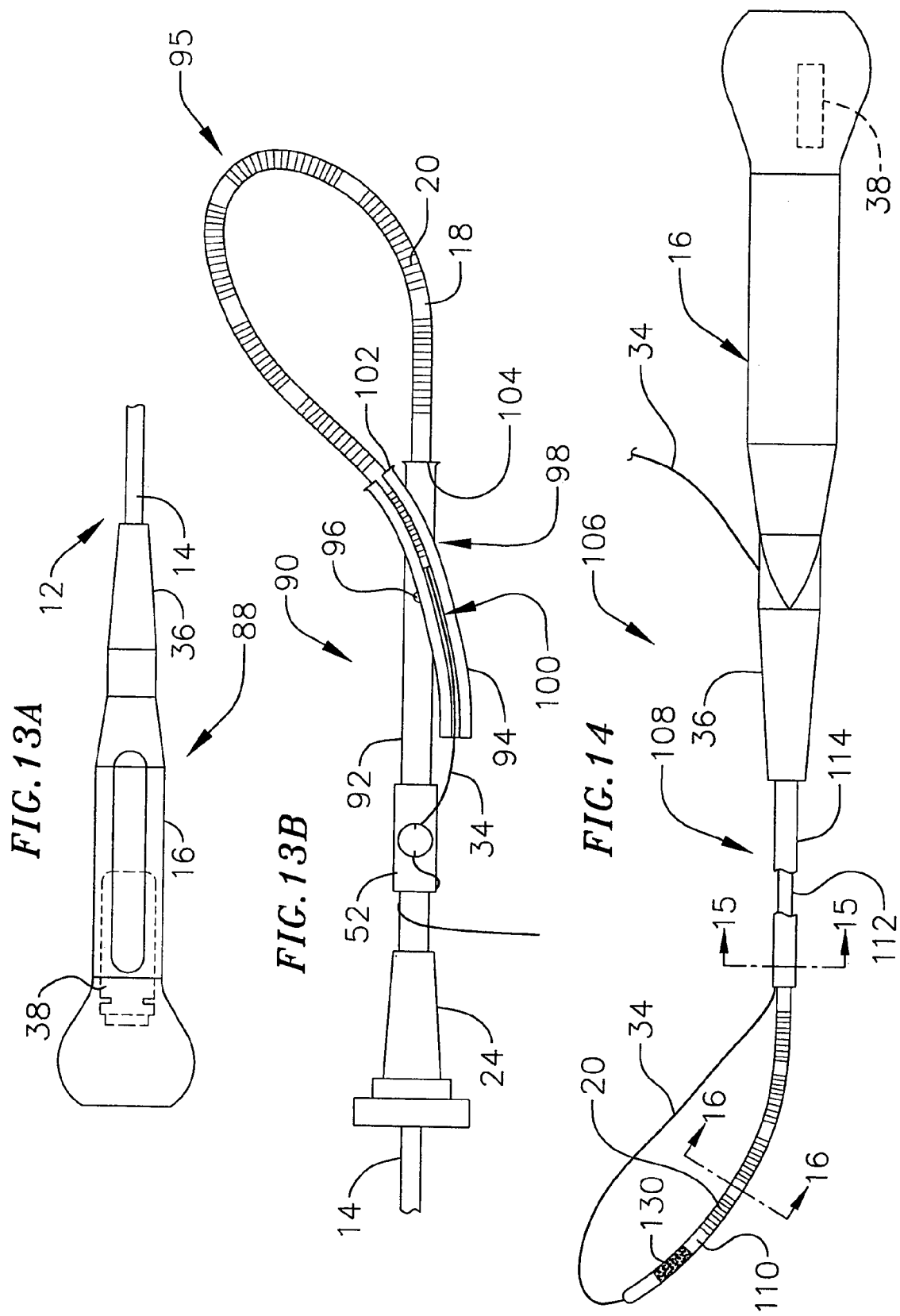

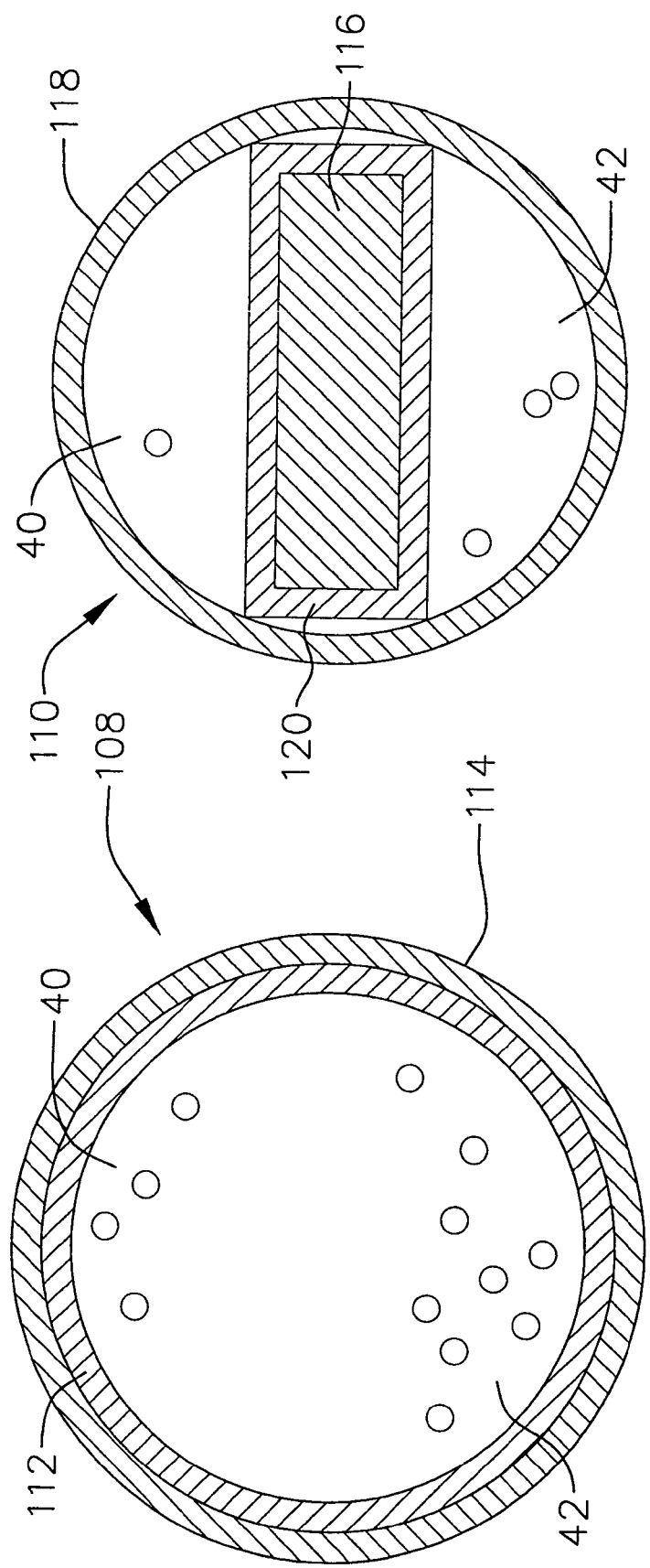

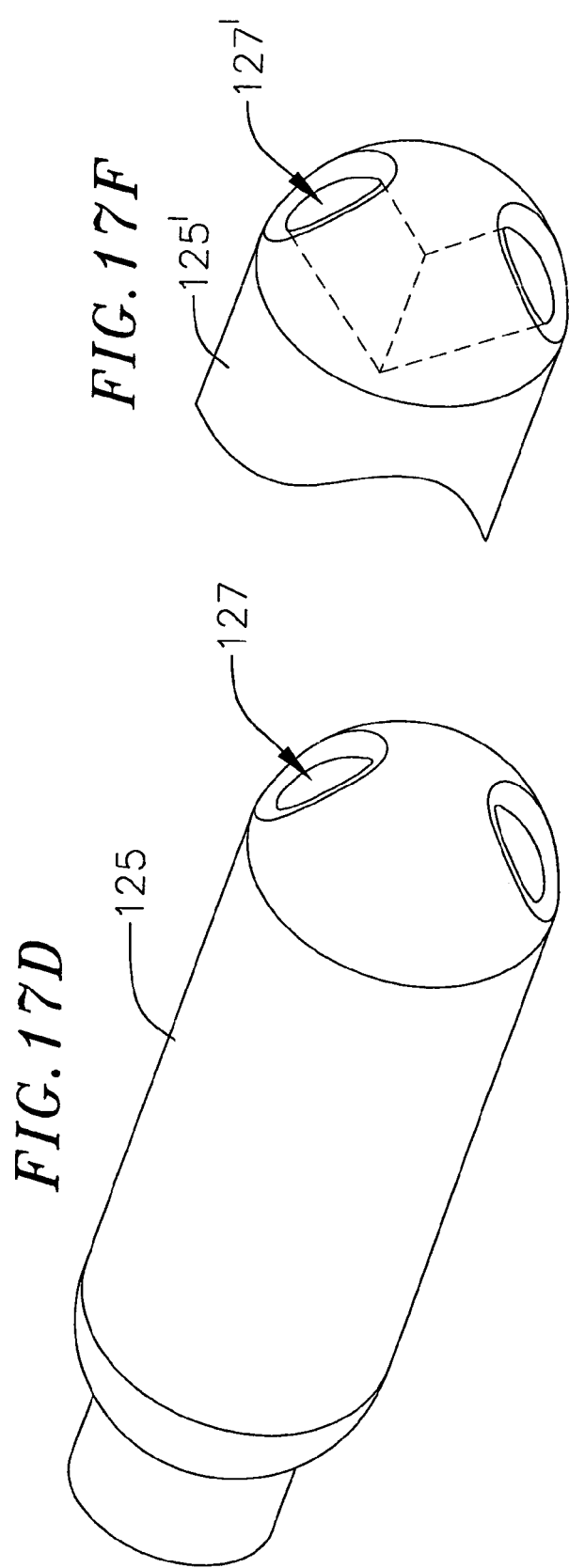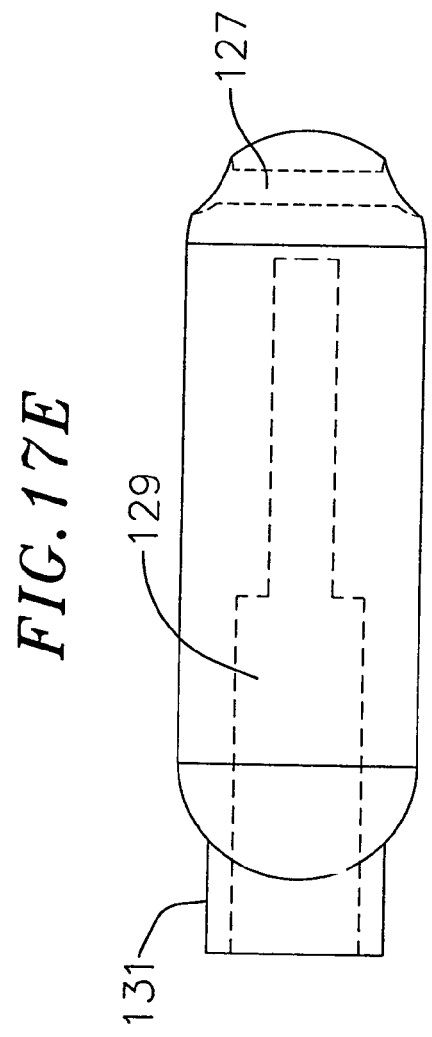

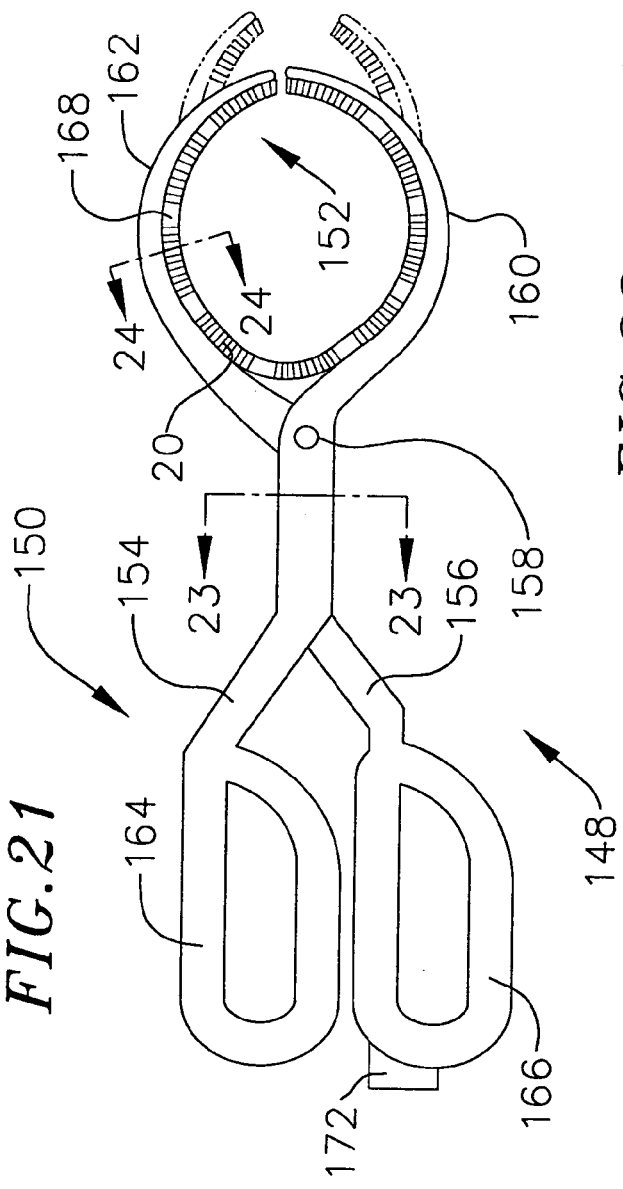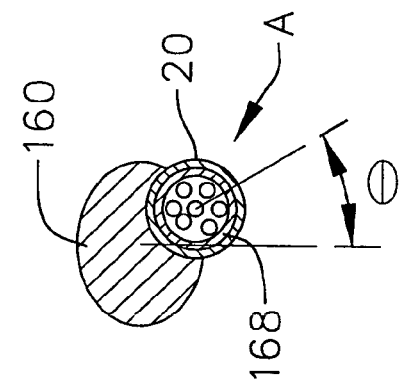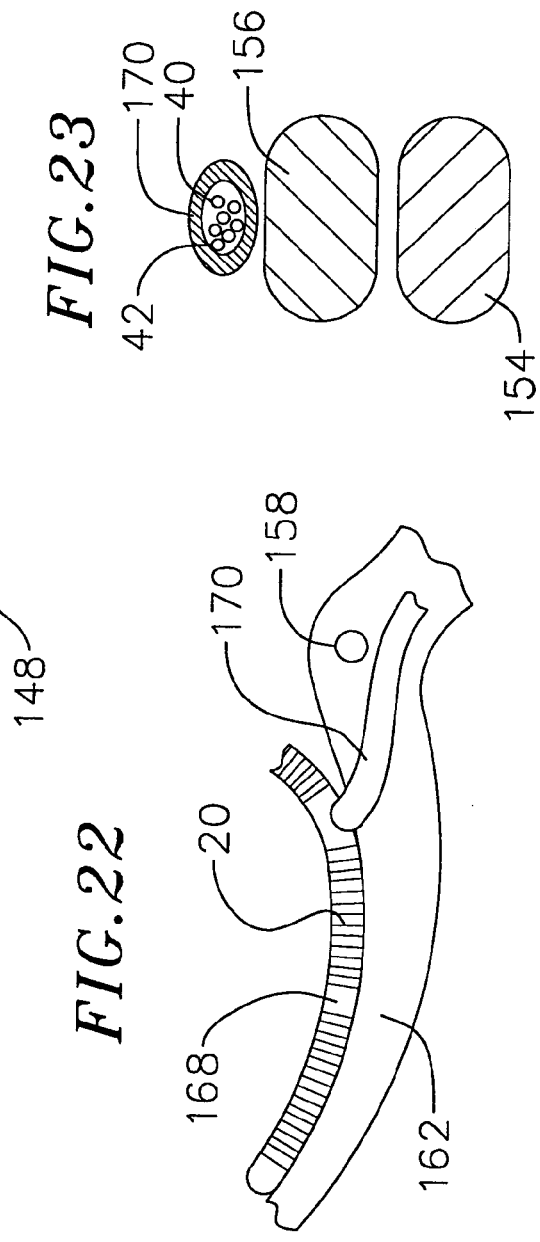

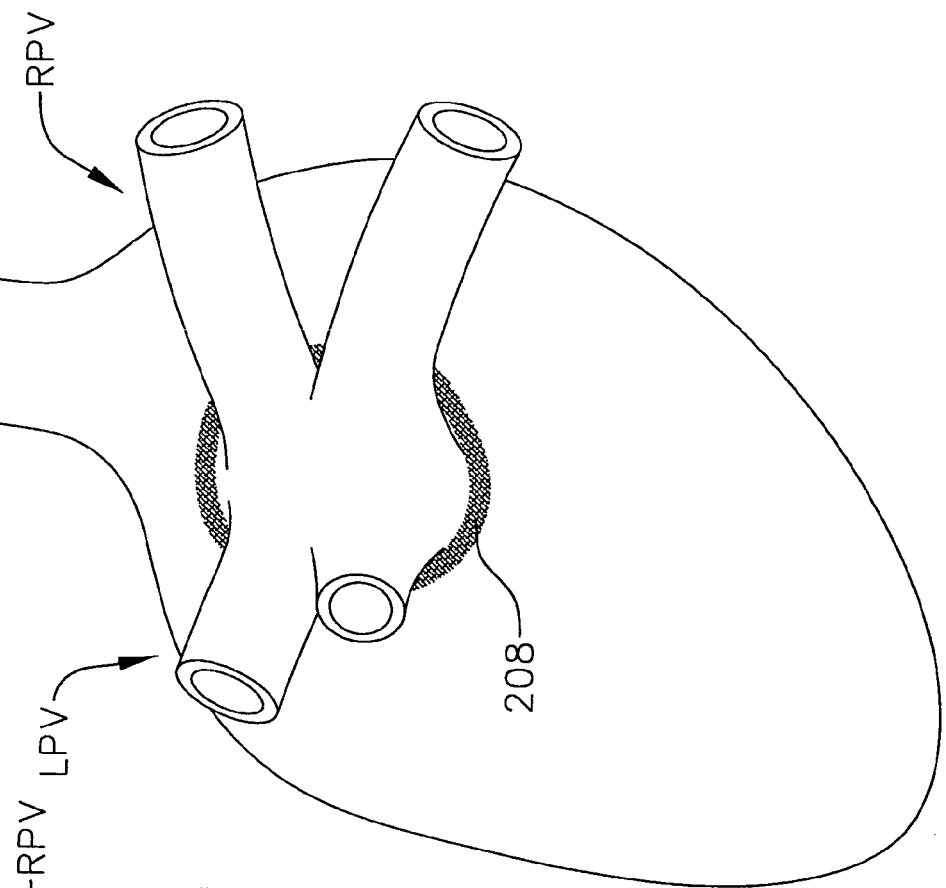
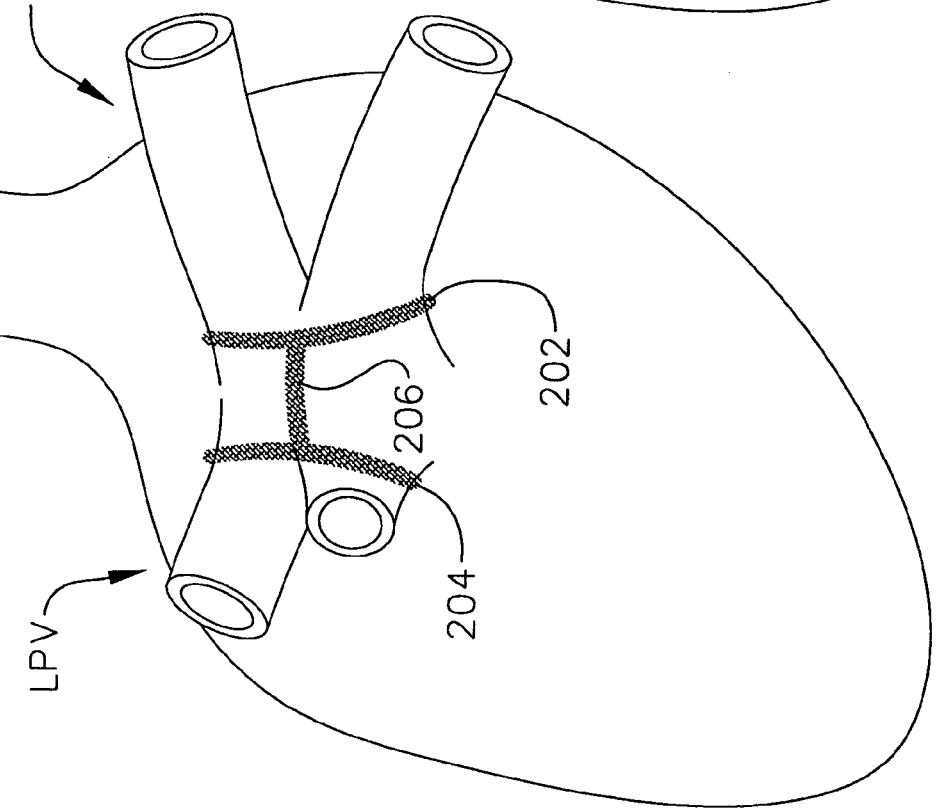

METHOD AND APPARATUS FOR POSITIONING A DIAGNOSTIC OR THERAPEUTIC ELEMENT WITHIN THE BODY AND TIP ELECTRODE FOR USE WITH SAME

CROSS-REFERENCE TO RELATED APPLICATIONS

This application is a continuation of U.S. application Ser. No. 09/534,713, filed Mar. 24, 2000, now U.S. Pat. No. 6,645,200, which is a continuation-in-part of U.S. application Ser. No. 09/072,872, filed May 5, 1998, now U.S. Pat. No. 6,142,994 which is a continuation-in-part of U.S. application Ser. No. 08/949,117, filed Oct. 10, 1997, now U.S. Pat. No. 6,152,920.

BACKGROUND OF THE INVENTIONS

1. Field of Inventions

The present inventions relate generally to structures for positioning diagnostic and therapeutic elements within the body and, more particularly, to devices which are particularly well suited for the treatment of cardiac conditions

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

Although pharmacological treatment is available for atrial fibrillation and flutter, the treatment is far from perfect. For example, certain antiarrhythmic drugs, like quinidine and procainamide, can reduce both the incidence and the duration of atrial fibrillation episodes. Yet, these drugs often fail to maintain sinus rhythm in the patient. Cardioactive drugs, like digitalis, Beta blockers, and calcium channel blockers, can also be given to control the ventricular response. However, many people are intolerant to such drugs. Anticoagulant therapy also combats thromboembolic complications, but does not eliminate them. Unfortunately, pharmacological remedies often do not remedy the subjective symptoms associated with an irregular heartbeat. They also do not restore cardiac hemodynamics to normal and remove the risk of thromboembolism.

Many believe that the only way to really treat all three detrimental results of atrial fibrillation and flutter is to actively interrupt all of the potential pathways for atrial reentry circuits.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive. Thus, despite its considerable clinical success, only a few maze procedures are done each year.

Maze-like procedures have also been developed utilizing catheters which can form lesions on the endocardium to effectively create a maze for electrical conduction in a predetermined path. Exemplary catheters are disclosed in commonly assigned U.S. Pat. No. 5,582,609. Typically, the lesions are formed by ablating tissue with an electrode carried by the catheter. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue.

Catheters used to create lesions (the lesions being 3 to 15 cm in length) typically include a relatively long and relatively flexible body portion that has an electrode on its distal end. The portion of the catheter body portion that is inserted into the patient is typically from 23 to 55 inches in length and there may be another 8 to 15 inches, including a handle outside the patient. The proximal end of the catheter body is connected to the handle which includes steering controls. The length and flexibility of the catheter body allow the catheter to be inserted into a main vein or artery (typically the femoral artery), directed into the interior of the heart, and then manipulated such that the electrode contacts the tissue that is to be ablated. Fluoroscopic imaging is used to provide the physician with a visual indication of the location of the catheter.

Catheter-based soft tissue coagulation has proven to be a significant advance in the medical arts generally and in the treatment of cardiac conditions in particular. Nevertheless, the inventors herein have determined that catheter-based procedures are not appropriate in every situation and that conventional catheters are not capable of reliably forming all types of lesions. One lesion that has proven to be difficult to form with conventional catheters is the circumferential lesion that is used to isolate a pulmonary vein and cure ectopic atrial fibrillation. Lesions that isolate the pulmonary vein may be formed within the pulmonary vein itself or in the tissue surrounding the pulmonary vein. These circumferential lesions are formed by dragging a tip electrode around the pulmonary vein or by creating a group of interconnected curvilinear lesions one-by-one around the pulmonary vein. Such techniques have proven to be less than effective because they are slow and gaps of conductive tissue can remain after the procedure. It can also be difficult to achieve adequate tissue contact with conventional catheters.

Endocardial lesions to isolate pulmonary veins have also been formed as a secondary procedure during a primary open heart surgical procedure such as mitral valve replacement. A surgical soft tissue coagulation probe is used to form the endocardial lesions after the heart has been opened, either before or after the valve replacement. This technique does, however, increase the amount of time the patient is on pulmonary bypass, which can be undesirable.

Accordingly, the inventors herein have determined that a need exists for surgical methods and apparatus that can be used to create lesions around bodily structures and, in the context of the treatment of atrial fibrillation, around a pulmonary vein without increasing the amount of time that the patient is on pulmonary bypass.

SUMMARY OF THE INVENTIONS

Accordingly, the general object of the present inventions is to provide methods and apparatus that avoid, for practical purposes, the aforementioned problems. In particular, one object of the present inventions is to provide surgical methods and apparatus that can be used to create lesions around a pulmonary vein or other body structure in a more efficient manner than conventional apparatus. Another object of the present inventions is to provide surgical methods and apparatus that may be used to create lesions around a pulmonary vein without placing the patient on pulmonary bypass or increasing the amount of time that the patient is on pulmonary bypass when a related procedure is being performed. Still another object of the present inventions is to perform a diagnostic or therapeutic procedure, such as the coagulation of tissue around a body structure, without effecting collateral tissue that is not targeted for the procedure.

In order to accomplish some of these and other objectives, a surgical device in accordance with a present invention includes a relatively short outer member, a relatively short shaft located at least partially within the relatively short outer member and slidable relative to the relatively short outer member, and an operative element on the distal portion of the relatively short shaft. The distal portion of the relatively short shaft is adapted to be connected to the distal portion of the relatively short outer member such that the distal portion of the shaft member will form a loop.

In order to accomplish some of these and other objectives, a surgical device in accordance with a present invention includes a relatively short outer member, a relatively short shaft located at least partially within the relatively short outer member and slidable relative to the relatively short outer member, a control element defining a distal portion connected to the distal portion of the relatively short shaft and a proximal portion extending toward the proximal portion of the relatively short outer member, and an operative element on the distal portion of the relatively short shaft. The distal portion of the relatively short shaft may be used to form a loop.

In order to accomplish some of these and other objectives, a surgical; device in accordance with a preferred embodiment of a present invention includes a relatively short shaft and a distal member having a flexible region and a malleable region and an operative element carried by the distal member. Preferably, the distal tip assembly may, if desired, also include a pull wire that facilitates the formation of a loop.

In order to accomplish some of these and other objectives, a clamp device in accordance with a preferred embodiment of a present invention includes first and second curved members and a tissue coagulation apparatus associated with the first and second curved members. The curved members and tissue coagulation apparatus preferably together define an open region that may be positioned around a body structure such as one or more pulmonary veins.

Such devices provide a number of advantages over the conventional devices used to create lesions around pulmonary veins. For example, the operative element carrying loops and the first and second curved members may be positioned around a pulmonary vein (or veins) on the epicardial surface in accordance with inventive methods disclosed herein. A continuous transmural lesion that will isolate the vein may then be created while the heart is beating. The heart need not be opened and pulmonary bypass is not required. As such, the present devices advantageously allow curative lesions to be formed around pulmonary veins without the difficulties associated with catheter-based procedures or the time on pulmonary bypass required by conventional surgical procedures.

In order to accomplish some of these and other objectives, a mask element for masking an operative element supported on a support body in accordance with a present invention includes a main body with a side wall defining an interior bore and a side wall opening. The mask element, which is preferably formed from thermally and electrically insulating material, is adapted to be positioned on the support structure such that a portion of the operative element is aligned with the side wall opening and a portion of the operative element is covered by the side wall. When the support structure is positioned with the side wall opening (and exposed portion of the operative element) facing the target tissue region, the remainder of the operative element will be covered by the side wall. As such, the present mask element protects non-target collateral tissue from being damaged, sensed or otherwise affected by the operative element.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 10 is a side, partial section view of a pull wire guide and electrode support structure in accordance with a preferred embodiment of a present invention.

FIG. 11 is a perspective view of the pull wire guide illustrated in FIG. 10.

FIG. 12 is a perspective view of a pull wire guide in accordance with a preferred embodiment of a present invention.

FIGS. 13A and 13B are partial plan views together showing a surgical device in accordance with a preferred embodiment of a present invention.

FIG. 14 is a plan view of a surgical device in accordance with a preferred embodiment of a present invention.

FIG. 15 is a section view taken along line 15—15 in FIG. 14.

FIG. 16 is a section view taken along line 16—16 in FIG. 14.

FIG. 17D is a perspective view of a tip electrode in accordance with a preferred embodiment of a present invention.

FIG. 17E is a side view of the tip electrode illustrated in FIG. 17D.

FIG. 17F is a partial perspective view of another tip electrode.

FIG. 21 is a front plan view of a clamp device in accordance with a preferred embodiment of a present invention.

FIG. 22 is an enlarged rear plan view of a portion of the clamp device illustrated in FIG. 21.

FIG. 23 is a section view taken along line 23—23 in FIG. 21.

FIG. 24 is a section view taken along line 24—24 in FIG. 21.

FIG. 26 is a perspective view of a portion of a heart with lesions formed in accordance with a therapeutic method in accordance with a present invention.

FIG. 27 is a perspective view of a portion of a heart with a lesion formed in accordance with a therapeutic method in accordance with a present invention.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
 I. Loop Structures With Coupling Devices
 II. Loop Structures With Coupling Devices And Pull Wires
 III. Loop Structures With Pull Wires
 IV. Operative Elements, Temperature Sensing And Power Control
 V. Operative Element Identification
 VI. Masking
 VII. Clamp Devices
 VIII. Methods The section titles and overall organization of the present detailed description are for the purpose of convenience only and are not intended to limit the present inventions.

This specification discloses a number of structures, mainly in the context of cardiac ablation, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs.

I. Loop Structures with Coupling Devices

Figure 1A:
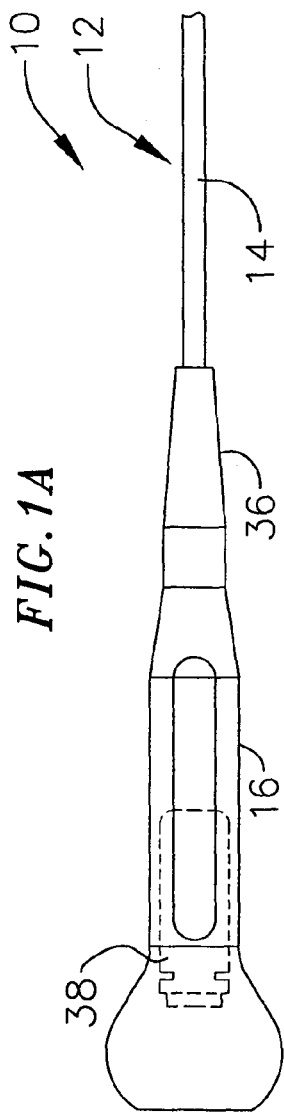
FIGS. 1A and 1B are partial plan views together showing a surgical device in accordance with a preferred embodiment of a present invention.
Figure 1B:
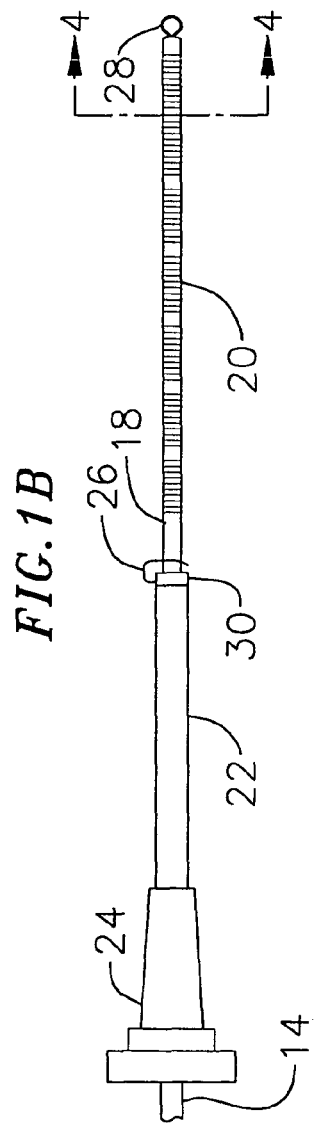

As illustrated for example in FIGS. 1A and 1B, a surgical device 10 in accordance with a preferred embodiment of a present invention includes a shaft 12 that is preferably formed from two tubular parts, or members. The proximal member 14 is attached to a handle 16 while the distal member 18, which is shorter than the proximal member, carries an operative element such as the illustrated plurality of spaced electrodes 20. The proximal member 14 is typically formed from a biocompatible thermoplastic material that is thermally and electrically insulating, such as a Pebax® material (polyether block amide). The distal member 18 is typically formed from a softer, more flexible biocompatible thermoplastic material that is also thermally and electrically insulating, such as Pebax® material, polyethylene, or polyurethane. The proximal and distal members, which are about 5 French to about 9 French in diameter, are preferably either bonded together with an overlapping thermal bond or adhesively bonded together end to end over a sleeve in what is referred to as a "butt bond."

The shaft 12 in the exemplary surgical device 10 extends through the interior bore of an outer member 22 in the manner illustrated in FIGS. 1A and 1B. The outer member 22 is preferably a tubular structure that includes a locking device 24, such as the illustrated Toughy Borst fitting, at the proximal end to fix the position of the shaft 12 relative to the outer member. The outer member 22 also preferably includes a flared inner surface 23 (FIG. 2) to facilitate movement of the electrodes 20 into the outer member. Alternatively, the distal end of the outer member may be formed from relatively soft material. With respect to materials the outer member 22 may be formed from a thermally and electrically insulating biocompatible thermoplastic material such as Pebax® material.

The shaft 12 and outer member 22 are both relatively short. The term "relatively short" is used in the present specification to describe a length that is suitable for direct placement against the targeted tissue region during a surgical procedure. "Relatively long" shafts, on the other hand, include conventional catheter shafts that are guided through the vasculature to a target tissue region. In the context of the surgical procedures involving the heart, access to the targeted tissue region may be obtained by way of a thoracotomy, median sternotomy, or thoracostomy. As such, the length of the shaft 12 is preferably between about 6 inches and about 30 inches, with the proximal member 14 being between about 3 inches and about 20 inches, and the distal member 18 being between about 3 inches and about 20 inches. The length of the outer member 22 is only about 2 inches to about 10 inches.

Figure 4:
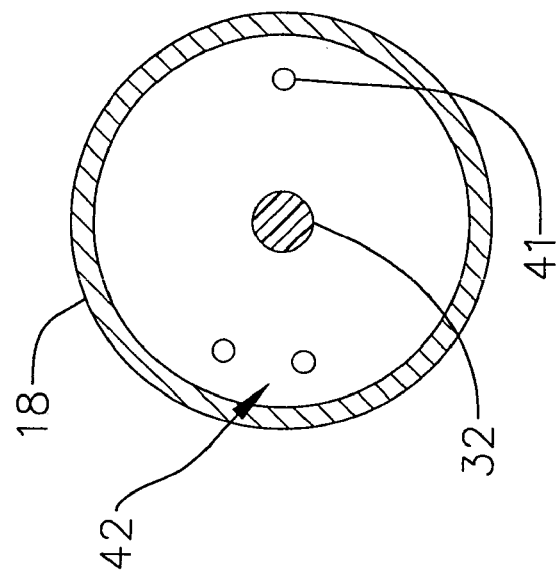
FIG. 4 is a section view taken along line 4—4 in FIG. 1B.
Figure 3:
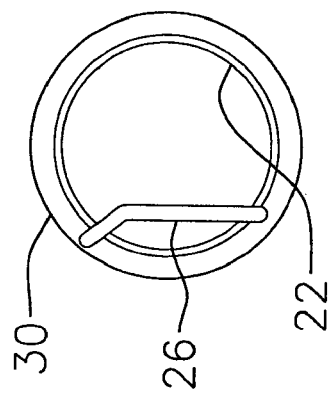
FIG. 3 is an end view of the outer member illustrated in FIG. 1B.
Figure 2:
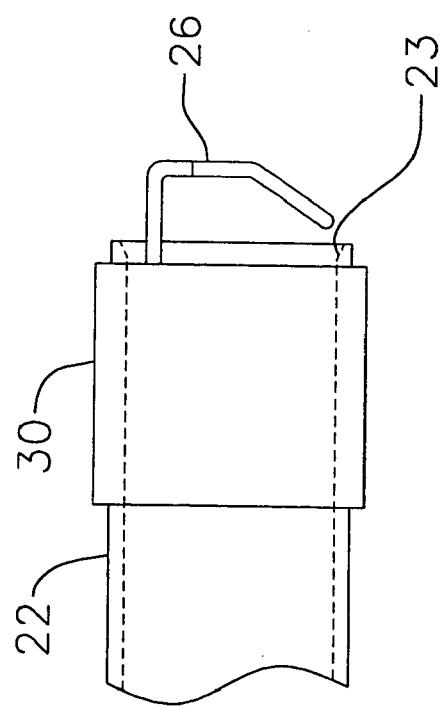
FIG. 2 is a side view of the outer member illustrated in FIG. 1B.

A loop may be formed by securing the distal end of the shaft 12 to the distal end of the outer member 22 and a fastening apparatus is provided that allows the distal ends to be releasably secured to one another. The fastening apparatus in the illustrated embodiment consists of a hook 26 on the distal end of the outer member 22 and an eyelet 28 on the distal end of the shaft 12. Referring more specifically to FIGS. 2 and 3, the hook 26 is mounted on a cylindrical base 30 that is itself mounted on the exterior of the distal end of the outer member 22. The base 30, which along with the hook 26 is preferably formed from metal or plastic, may be secured to the outer member 22 through the use of adhesive, welding or other suitable methods. The eyelet 28 is anchored to a flexible internal core wire 32 (FIG. 4) that may be formed from resilient inert wire, such as stranded or solid nickel titanium (commercially available under the name Nitinol), braided Spectran® or Kevlar® fibers, or common suture materials. Suitable materials for the eyelet 28 include Nitinol, 17–7 stainless steel, Spectran® and Kevlar®. It should also be noted that the locations of the hook 26 and eyelet 28 may be reversed.

Figure 1C:
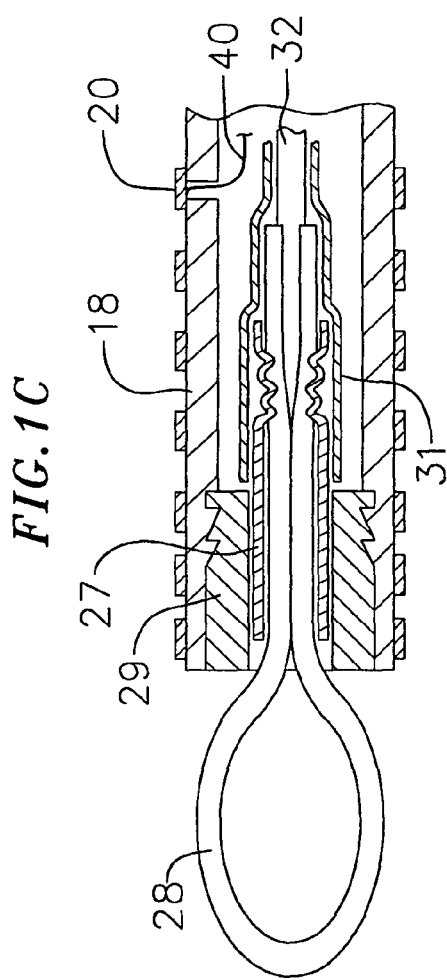
FIG. 1C is a partial section view of the distal portion of the shaft illustrated in FIG. 1B.

The core wire 32 is anchored at the proximal end of the shaft 12, while the core wire and eyelet 28 are both anchored at the distal end of the shaft. Referring to FIG. 1C, the proximal portion of the eyelet 28 and the distal portion of the core wire 32 are secured to one another with a crimp tube 27 in the exemplary embodiment. The crimp tube 27 is soldered, welded or otherwise bonded to a tip anchor 29 that is mounted on the distal end of the distal member 18. An insulating sleeve 31 is also provided along the length of the distal member 18.

Although the core wire 32 is preferably circular in cross-section, the portion of the core wire within the distal member 18 may have a rectangular (or other non-circular shape) cross-section in order to control the bending plane of the distal member. This technique is especially useful when portions of the electrodes 20 are masked using one of the techniques described in Section VI below.

Figure 5:
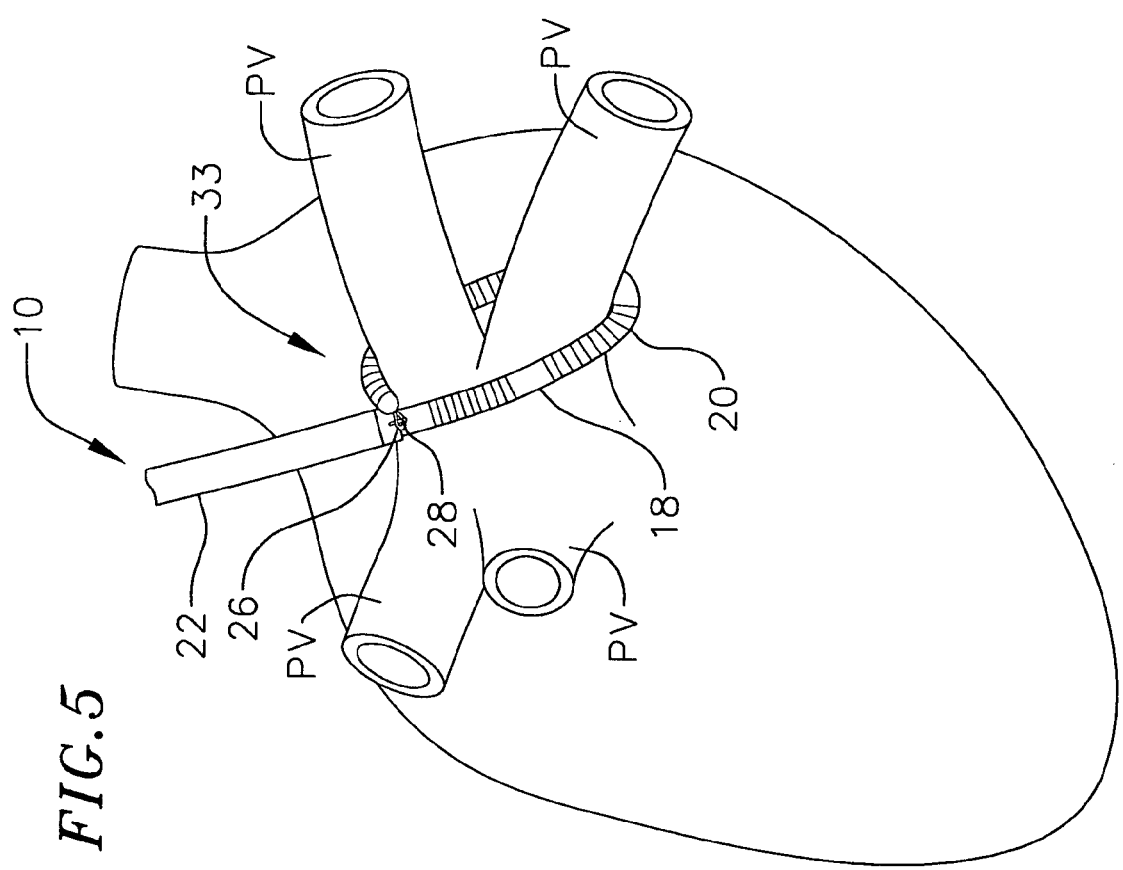
FIG. 5 is a perspective view showing the surgical device illustrated in FIGS. 1A–1C being used in a surgical procedure involving the heart.

As illustrated for example in FIG. 5, one use of the exemplary surgical device 10 involves the creation of an epicardial lesion around a pair of pulmonary veins PV. The shaft 12 and outer member 22 are directly inserted into the patient's chest and the shaft distal member 18 may be threaded around a pair of pulmonary veins PV with hemostats or other surgical instruments. An adjustable loop 33 is formed by placing the eyelet 28 over the hook 26. The loop 33 may be tightened around the pulmonary veins PV by holding the outer member 22 and pulling the shaft 12 in the proximal direction. Relative movement of the shaft 12 and outer member 22 can be prevented with the locking device 24 to maintain the loop 33 in the desired size. Once the loop 33 has been accurately positioned, some or all of the electrodes 20 may be used to create a transmural epicardial lesion around the pulmonary veins PV. Additional information concerning methods of creating epicardial lesions is provided in Section VIII below.

In order to allow the distal member 18 to be tightly threaded around a relatively small structure such as a pulmonary vein, the distal member is preferably very flexible. As used herein, the term "very flexible" refers to distal members which are more flexible than the distal portions of conventional diagnostic and steerable electrophysiology catheters, which must be stiff enough to force electrodes against tissue.

The exemplary handle 16 illustrated in FIG. 1A consists of two molded handle halves and is provided with strain relief element 36 and a PC board 38. As discussed in greater detail in Section IV below, there is a temperature sensor associated with each longitudinal edge of the electrodes 20 in the illustrated embodiment. Signal wires 41 (FIG. 4) are connected to the electrodes 20 and signal wires 42 are connected to the temperature sensors. The signal wires are passed in conventional fashion through a lumen extending through the shaft 12 to the PC board 38. The PC board 38 is, in turn, electrically coupled to a connector that is received in a port at the proximal end of the handle 16. The connector plugs into a source of RF coagulation energy.

Figure 6A:
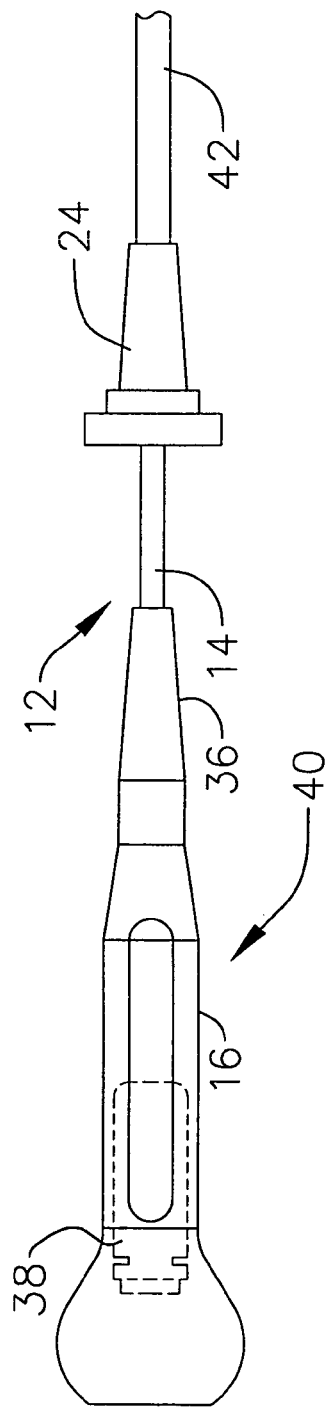
FIGS. 6A and 6B are partial plan views together showing a surgical device in accordance with a preferred embodiment of a present invention.
Figure 6B:
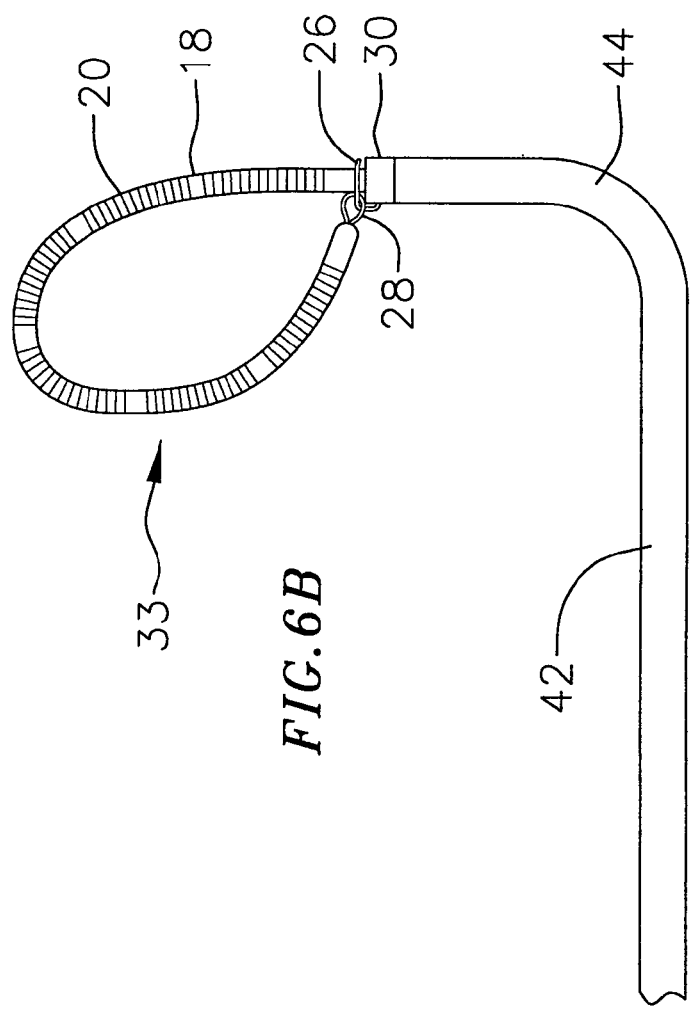

Another exemplary device, which is generally represented by reference numeral 40, is illustrated in FIGS. 6A and 6B. Many structural elements in the exemplary device 40 are similar to those in the exemplary device 10 and such elements are represented by the same reference numerals. For example, the exemplary device 40 includes a relatively short shaft 12 with a proximal member 14 and a distal member 18 that supports a plurality of electrodes 20 or some other operative element. Exemplary device 40 also includes a handle 16 and a hook 26 and eyelet 28 arrangement.

The primary difference between the two surgical devices is that the exemplary device 40 includes a relatively short outer member 42 that is relatively stiff. In other words, the outer member is either rigid, malleable, or somewhat flexible. A rigid outer member cannot be bent. A malleable outer member is a outer member that can be readily bent by the physician to a desired shape, without springing back when released, so that it will remain in that shape during the surgical procedure. Thus, the stiffness of a malleable outer member must be low enough to allow the outer member to be bent, but high enough to resist bending when the forces associated with a surgical procedure are applied to the outer member. A somewhat flexible outer member will bend and spring back when released. However, the force required to bend the outer member must be substantial. Rigid and somewhat flexible shafts are preferably formed from stainless steel, while malleable shafts are formed from annealed stainless steel. Additional information concerning malleable structures may be found in aforementioned U.S. application Ser. No. 09/072,872.

A rigid or somewhat flexible outer member 42 may be linear or formed with one or more bends 44 designed for a particular surgical procedure, as is illustrated for example in FIG. 6B. The physician may place bends in a malleable outer member 42 in order to facilitate proper placement of the distal end of the outer member.

II. Loop Structures with Coupling Devices and Pull Wires

It may be difficult in some instances to thread the shaft distal member 18 around an anatomical structure such as a pulmonary vein. As such, the distal end of the shaft 12 may be provided with a pull wire 34, as is illustrated for example FIG. 7A. The pull wire 34, which is thinner and more flexible than the shaft distal member 18, will be easier to thread around anatomical structures. After the pull wire 34 has been threaded around a pulmonary vein or other structure, and around the hook 26, the pull wire may be used to pull the shaft distal member 18 around the structure to form a loop. Suitable materials for the pull wire 34, which is typically more flexible than the core wire 32, include stranded Nitinol, Spectran® and Kevlar®.

Figure 7A:
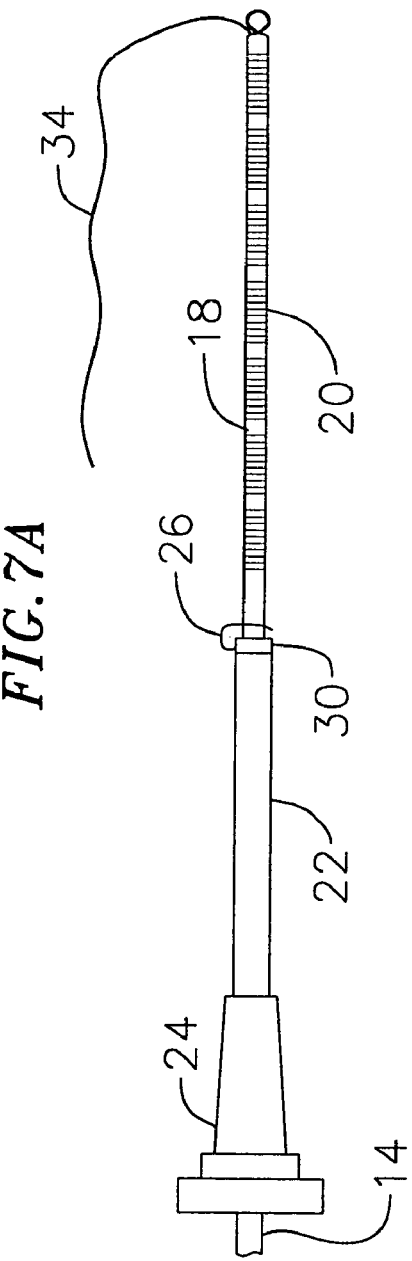
FIG. 7A is a plan view of a portion of a surgical device in accordance with a preferred embodiment of a present invention.
Figure 7B:
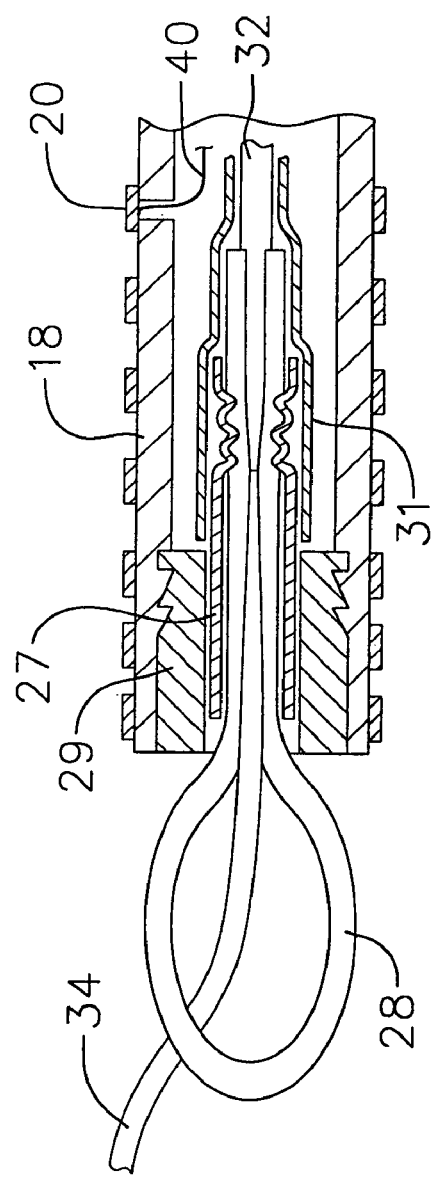
FIG. 7B is a partial section view of the distal portion of the shaft illustrated in FIG. 7A.

The pull wire 34 may be secured to the core wire 32 with a crimp tube or other suitable device in the manner illustrated, for example, in FIG. 7B. More specifically, the proximal portions of the eyelet 28 and pull wire 34 and the distal portion of the core wire 32 are secured to one another with a crimp tube 27. The crimp tube 27 is soldered, welded or otherwise bonded to a tip anchor 29 that is mounted on the distal end of the distal member 18.

III. Loop Structures with Pull Wires

Figure 8A:
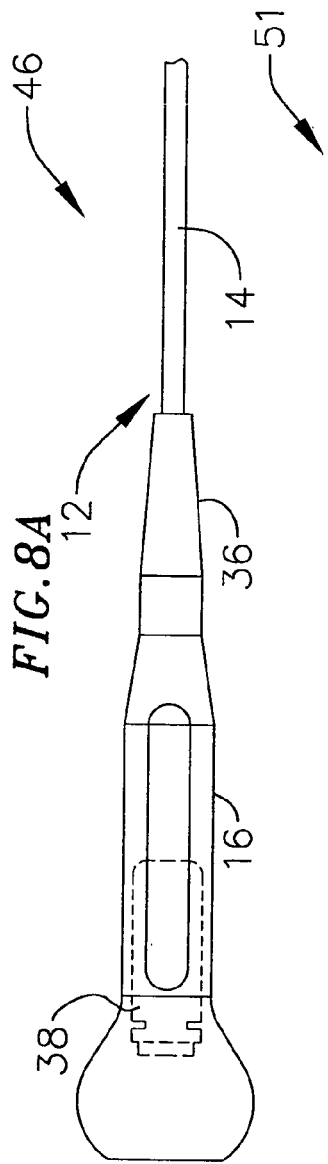
FIGS. 8A and 8B are partial plan views together showing a surgical device in accordance with a preferred embodiment of a present invention.
Figure 8B:
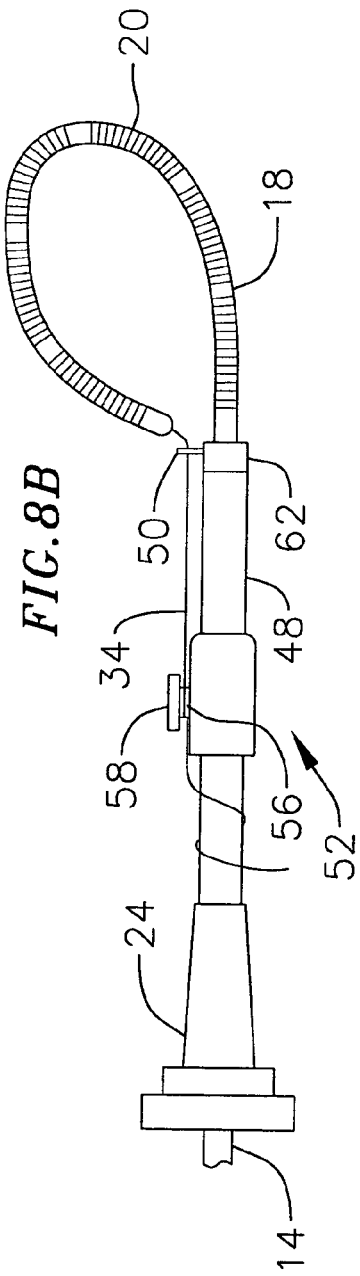

As illustrated for example in FIGS. 8A and 8B, a surgical device 46 in accordance with a preferred embodiment of a present invention includes many structural elements similar to those in the exemplary devices illustrated in FIGS. 1A–7B and such elements are represented by the same reference numerals. For example, the exemplary surgical device 46 includes a relatively short shaft 12 with a proximal member 14 and a distal member 18 that supports a plurality of electrodes 20 or some other operative element. The proximal end of the shaft 12 is secured to a handle 16.

Figure 8C:
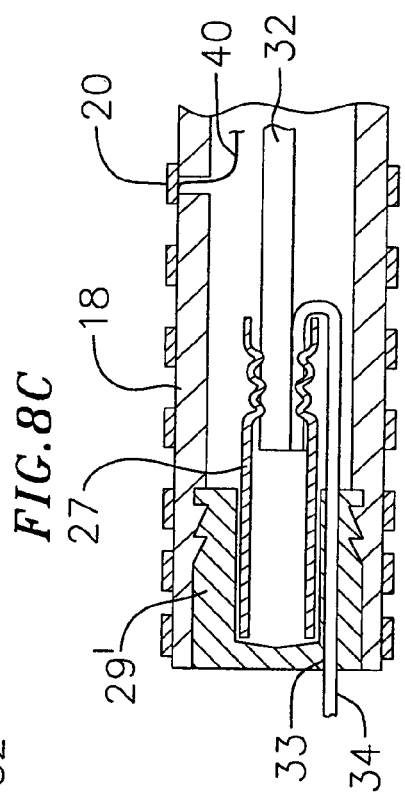
FIG. 8C is a partial section view of the distal portion of the shaft illustrated in FIG. 8B.

As illustrated for example in FIG. 8C, a pull wire 34 similar to that illustrated in FIGS. 7A and 7B is crimped to the core wire 32 with a crimp tube 27 and the crimp tube is secured to a tip anchor 29' by bonding, welding or other suitable methods. Here, however, the tip anchor 29' has a closed distal end and the pull wire 34 is threaded through an opening 33 in the anchor. Alternatively, the core wire 32 and pull wire 34 may be replaced with a single, continuous pull/core wire (not shown).

The exemplary surgical device 46 does not, however, include an outer member with a coupling device that secures the distal portion of the outer member to the shaft distal member 18. Instead, surgical device 46 includes a relatively short outer member 48 with a pull wire guide 50. The outer member 48 also includes a flared inner surface (not shown) or soft material at its distal end and a locking device 24, such as a Toughy Borst fitting, at its proximal end to fix the position of the shaft 12. The pull wire 34 may be threaded through the pull wire guide 50 to form a loop 51 and then secured to an anchoring device 52. The loop 51 may then be adjusted by moving the shaft 12 and outer member 48 relative to one another or by adjusting the pull wire 34. In one exemplary procedure, the pull wire 34 will be threaded around a pair of pulmonary veins prior to being threaded through the pull wire guide 50 to form a loop similar to that illustrated in FIG. 5.

With respect to the physical characteristics of the outer member 48, the outer member is preferably formed from relatively high durometer materials (72D and above) such as braided or unbraided Pebax® or Nylon material that is stiffer than the distal member 18 as well as thermally and electrically insulating. The outer member 48 should also be slightly shorter (i.e. 1 to 2 inches shorter) than the proximal member 14.

Figure 9B:
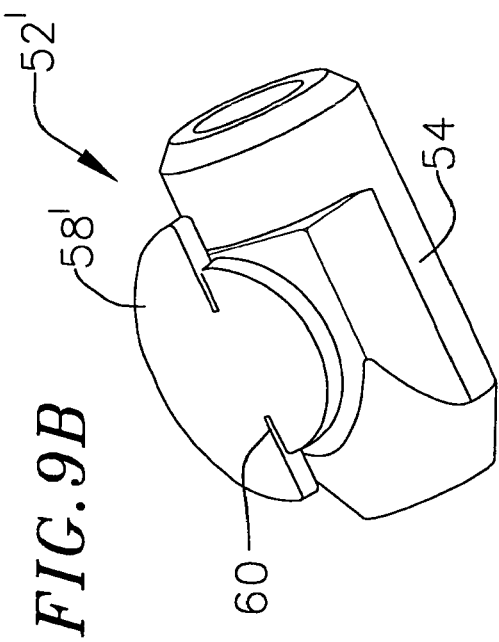
FIGS. 9B–9D are perspective views of other exemplary anchoring devices.
Figure 9D:
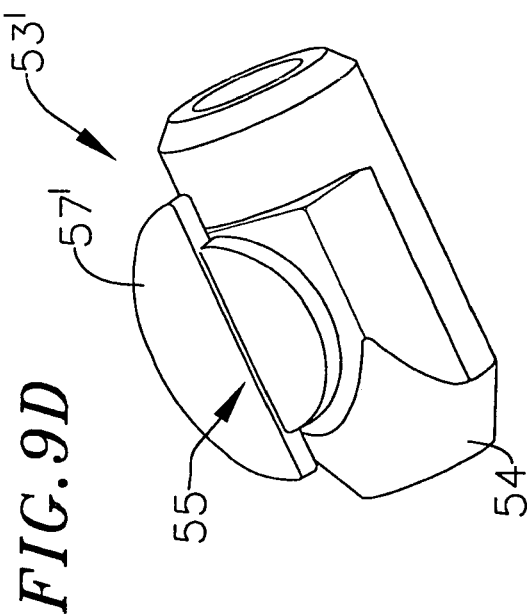
Figure 9A:
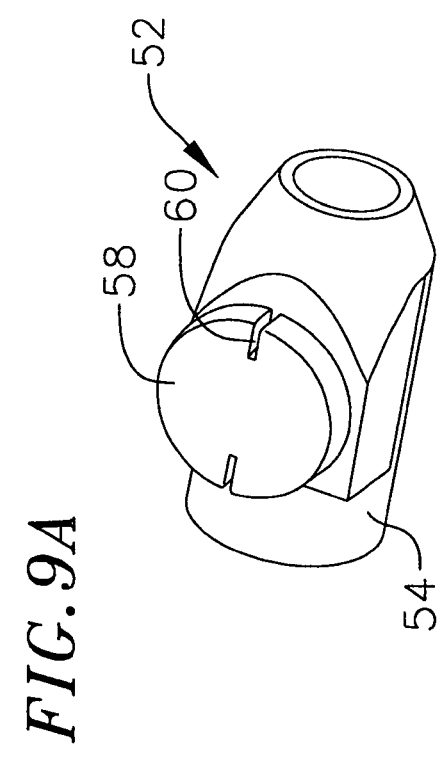
FIG. 9A is a perspective view of the exemplary anchoring device illustrated in FIG. 8B.
Figure 9C:
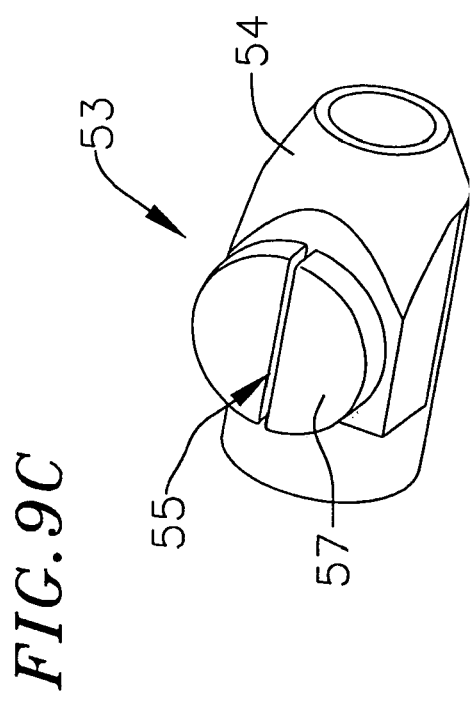

As illustrated in FIGS. 8B and 9A, the exemplary anchoring device 52 includes a main body 54 that is mounted on the outer member 48, a post 56 and a cap 58. The cap 58 includes a pair of slots 60. The pull wire 34 is wound around the post 56 and then through the slots 60 to anchor it in place. The anchoring device 52 is preferably formed from molded plastic. An alternate anchoring device 52', with a slightly differently shaped cap 58', is illustrated in FIG. 9B. Still other anchoring devices, which are represented by reference numerals 53 and 53', are illustrated in FIGS. 9C and 9D. Here, slots 55 extend through caps 57 and 57' and into the posts 56 on which the caps are mounted. The flexibility of the plastic material allows the pull wire 34 to be pulled down through into slot 55 and then held in place through friction and mechanical interference.

In the exemplary embodiment illustrated in FIGS. 8A–8C, the pull wire guide 50 is an eyelet or other simple loop or hook structure formed from metal or plastic that is mounted on a cylindrical base 62. Alternatively, as illustrated in FIGS. 10 and 11, a pull wire guide 64 may be provided with a plurality of pull wire openings 66 that extend around the periphery of the distal end of the outer member 48. This arrangement facilitates the threading of a pull wire through the pull wire guide 64 regardless of the rotational orientation of the outer member 48 relative to the physician and patient and also eliminates the need for the rotational orientation to be closely monitored and/or adjusted prior to loop formation.

The exemplary pull wire guide 64 illustrated in FIGS. 10 and 11, which may be formed from metal or plastic, includes a base 68 and an outwardly flared member 70 in which the openings 66 are located. The base 68 has a mounting surface 72 with a shape corresponding to that of the outer member on which it is mounted, i.e. cylindrical in the illustrated embodiment, and a smooth curved lip 74 that should extend inwardly from the mounting surface a distance that is at least equal to the wall thickness of the outer member. The flared member 70 includes a plurality of supports 75 and a peripheral ring 76 that together define the pull wire openings 66. The flared member 70 also has a smooth inner surface 78 that, together with the smooth curved lip 74, facilitates movement of the electrodes 20 or other operative elements through the pull wire guide 64 and into the outer member 48.

Turning to FIG. 12, the exemplary pull wire guide 80 illustrated therein is substantially similar to the guide illustrated in FIGS. 10 and 11 and similar structural elements are represented by similar reference numerals. Here, however, the peripheral ring 76 in the flared member 70 has been replaced by a plurality of a peripheral members 82 in a flared member 70' that define slots 84 therebetween. The slots 84 allow a pull wire to be slipped into the openings 66 instead of threaded through the openings. The peripheral members 82 also include curved, inwardly extending end portions 86 that prevent the pull wire from sliding out of the openings 66 once it is located therein.

Another exemplary surgical device, which is generally represented by reference numeral 88, is illustrated in FIGS. 13A and 13B. Like the exemplary surgical device 46 illustrated in FIGS. 8A–8C, surgical device 88 includes a shaft 12, with a proximal member 14 secured to handle 16 and a distal member 18 that supports electrodes 20 or some other operative element, and a pull wire 34. However, instead of a single relatively short outer member, surgical device 88 includes an outer member assembly 90 with a pair of outer members 92 and 94. A loop 95 is formed by directing the shaft distal member 18 outwardly from the distal end of outer member 92 and into the distal end of the outer member 94. The pull wire 34 may be anchored with an anchoring member 52 and the shaft 12 held in place relative to the outer member 92 with a locking device 24. The outer members are preferably formed from stainless steel or molded polymer material and have a inner diameter of about 7 French and an outer diameter of about 10 French.

The configuration of the loop 95 formed by the distal member 18 is primarily determined by the shape and relative orientation of the outer members 92 and 94. In the illustrated embodiment, outer member 92 is linear and outer member 94 is curved. The outer members 92 and 94, which are held in place relative to one another by a post 96 and weld (not shown) in region 98, are oriented such that the distal ends thereof define an angle of about 45 degrees. Of course, the curvatures of the outer members 92 and 94, as well as the relative orientation thereof, may be adjusted to suit particular needs.

In order to facilitate formation and adjustment of the loop 95, outer member 94 includes a pull wire slot 100 and the distal ends of the outer members 92 and 94 respectively include outwardly flared portions 102 and 104. The pull wire slot 100 is wide enough to allow the pull wire 34 to slide into the outer member 94, yet too narrow to allow the shaft distal member 18 to slide out of the outer member once it has been pulled in. As such, loop 95 may be formed by advancing the shaft distal member 18 outwardly from the distal end of the outer member 92, pulling on the pull wire 34 to bend the distal member back in the proximal direction, sliding the pull wire into the pull wire slot 100, and pulling the distal member into the distal end of the outer member 94.

As illustrated for example in FIGS. 14–16, a surgical device 106 in accordance with another preferred embodiment includes a relatively short shaft 108, a handle 16, and a distal section 110. The shaft 108 consists of a hypo-tube 112, which is either rigid or relatively stiff (preferably malleable), and an outer polymer tubing 114 over the hypo-tube. The distal section 110 is preferably somewhat flexible, in that it will conform to a surface against which it is pressed and then spring back to its original shape when removed from the surface. Surgical device 106 also includes a pull wire 34. The pull wire 34 is pre-threaded between the hypo-tube 112 and outer tubing 114 and through an aperture in the handle. Alternatively, the pull wire 34 may be threaded through a pull wire guide in the manner described above.

Referring more specifically to FIGS. 15 and 16, the exemplary distal section 110 preferably includes a spring member 116, which is preferably either a solid flat wire spring (as shown), a round wire, or a three leaf flat wire Nitinol spring, that is connected to the distal end of the hypo-tube 112 by welding or a crimp tube. Other spring members, formed from materials such as 17–7 or carpenter's steel, may also be used. As noted above, signal wires 41 and 42 connect the electrode 20 and temperature sensor elements to the PC board 38. The spring member 116 and signal wires 41 and 42 are enclosed in a flexible body 118, preferably formed from Pebax® material, polyurethane, or other suitable materials. The spring member 116 may also be pre-stressed so that the distal tip is pre-bent. An insulating sleeve 120 may be placed between the spring member 116 and the lead wires 41 and 42 if desired.

Figure 17A:
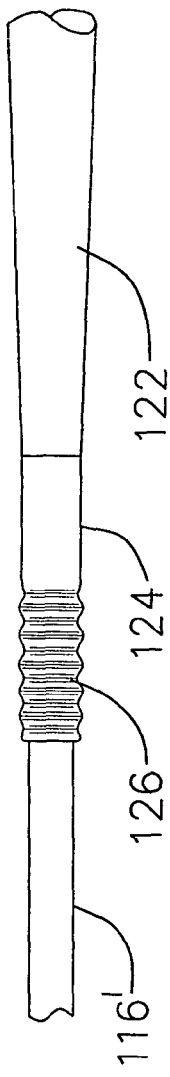
FIG. 17A is a partial side view of a distal structure that may be used in conjunction with a surgical device such as that illustrated in FIGS. 14 and 17C.

The distal section 110 may, alternatively, have a malleable portion. As illustrated for example in FIG. 17A, the spring member 116 (FIG. 16) is replaced with a shorter, but otherwise identical spring member 116' and a tapered malleable member 122 that is secured to the hypotube 112 by welding or other suitable methods. In a preferred implementation having seven electrodes, the malleable member 122 will extend to fourth electrode (counting proximal to distal), although this may be varied depending on the intended application. The spring member 116' and malleable member 122 may be secured to one another with a stainless steel crimp tube 124, which is soldered or otherwise bonded to the malleable member and mechanically coupled to the spring member with crimps 126. Suitable materials for the malleable member 122 include stainless steel.

Figure 17B:
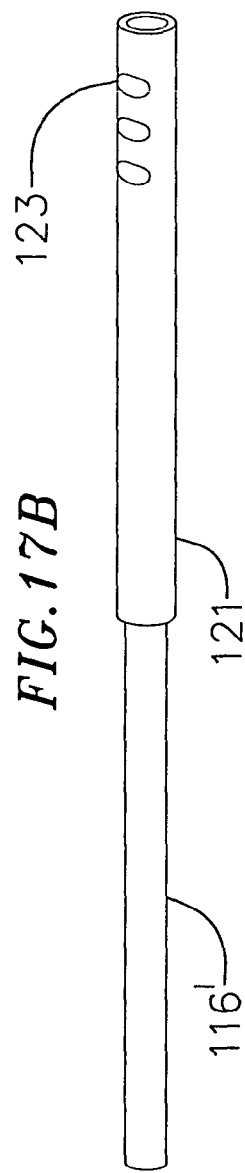
FIG. 17B is a side view of another distal structure that may be used in conjunction with a surgical device such as that illustrated in FIGS. 14 and 17C.

The malleable portion within the distal section 110 may also be provided in the manner illustrated in FIG. 17B. Here, the spring member 116' is secured to malleable hypotube 121 with, for example, crimps 123. The hypotube 121 is secured to the hypotube 112 by welding or other suitable methods. One particular advantage of this arrangement is that the relative lengths of the malleable and flexible regions may be varied during manufacture by simply varying the length of the hypotube 121.

Figure 17C:
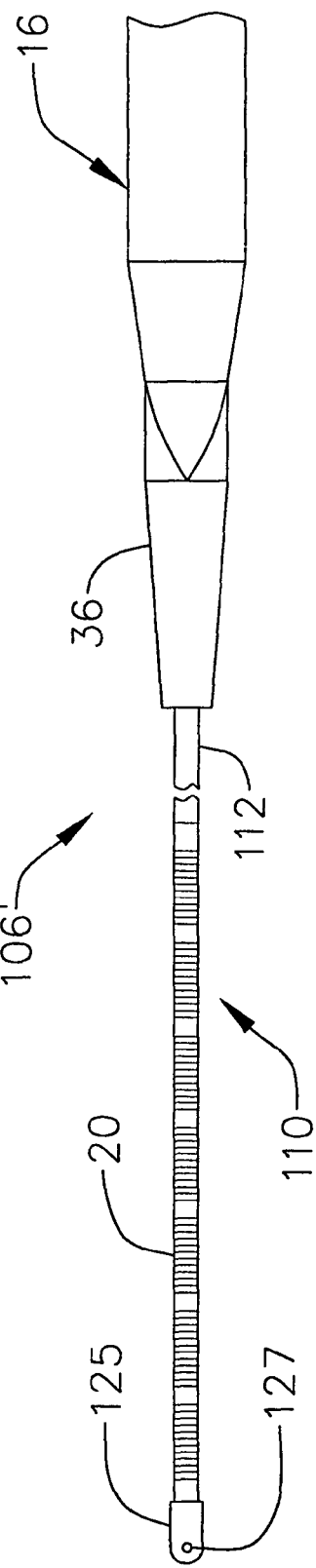
FIG. 17C is a plan view of a surgical device in accordance with a preferred embodiment of a present invention.

Probes having distal sections with both malleable and flexible regions may also be provided without a pull wire. The exemplary probe 106' illustrated in FIG. 17C is essentially identical to the probe 106 illustrated in FIG. 14. Here, however, the pull wire 34 and outer tubing 114 have been eliminated and a tip electrode 125 has been added.

Referring to FIGS. 17D and 17E, the tip electrode 125 preferably includes a through hole 127 that allows instrumentalities, such as suture material or one-quarter inch umbilical tape, to be threaded through the electrode to form a pull wire-like device if desired. The through hole 127 may also be engaged by a towel clamp formed from non-conducting material, or other similar device, during a procedure to allow the physician to push or pull from either end of the probe 106' for positioning and pressure application purposes. For example, after the suture material has been used to pull the probe 106' around an organ such as the heart, a towel clamp may be used to grab the distal end of the probe for more accurate positioning.

The ends of the through hole 127 are preferably chamfered and, as illustrated in FIG. 17E, the through hole may extend straight through the tip electrode 125. Alternatively, as illustrated in FIG. 17F, electrode 125' includes a through hole 127' with two portions arranged at an angle to one another. A lumen 129, having a large diameter portion and a small diameter portion (in which temperature sensors may be located), extends through the base 131 and into the interior of the tip electrode 125. The base 131 is inserted into the end of the distal section 110 during assembly.

It should be noted that a tip electrode with a through hole, such as those illustrated in FIGS. 17D–17F, may be used in combination with other probes, including those illustrated in FIGS. 1–13 of the present application. The exemplary electrodes illustrated in FIGS. 17C–17F have an outer diameter of about 2.7 mm and are about 8 mm in length. The size and shape of the tip electrode may, of course, be varied as desired to suit particular applications.

There are a number of advantages associated with probes having a distal section with both malleable and flexible regions. For example, the combination of malleable and flexible regions in the distal section 110 allows a single probe to form a wide variety of lesions. The relatively stiff, malleable region of the distal section 110 may be shaped to conform to anatomical structures on, for example, the surface of the heart. Direct pressure may then be applied to the structure during the formation of continuous lesions (note lesion 152 in FIG. 26) or segmented lesion patterns. The flexible region of the distal section 110 may be wrapped around anatomical structures such as, for example, pulmonary veins (note lesions 202 and 204 in FIG. 26). The malleable and flexible regions may also be used in conjunction with one another by, for example, shaping the malleable region to suit a particular procedure prior to wrapping the flexible region around an anatomical structure.

A probe with a combination of malleable and flexible regions in the distal section 110 may also be used in combination with the relatively short outer member 48 illustrated in FIG. 8B.

IV. Operative Elements, Temperature Sensing and Power Control

In each of the preferred embodiments, the operative element is a plurality of spaced electrodes 20. However, other operative elements, such as lumens for chemical ablation, laser arrays, ultrasonic transducers, microwave electrodes, and ohmically heated hot wires, and the like may be substituted for the electrodes.

The spaced electrodes 20 are preferably in the form of wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode is disclosed in U.S. Pat. No. 5,797,905.

As an alternative, the electrodes may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons. The electrodes can also be formed with a conductive ink compound that is pad printed onto a nonconductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The flexible electrodes 20 are preferably about 4 mm to about 20 mm in length. In the preferred embodiment, the electrodes are 12.5 mm in length with 1 mm to 3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

The electrodes 20 may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. The amount of power required to coagulate tissue ranges from 5 to 150 w.

As illustrated for example in FIG. 10, a plurality of temperature sensors 128, such as thermocouples or thermistors, may be located on, under, abutting the longitudinal end edges of, or in between, the electrodes 20. Preferably, the temperature sensors 128 are located at the longitudinal edges of the electrodes 20 on the side of the structure intended to face the tissue. In some embodiments, a reference thermocouple 130 (FIG. 14) may also be provided. For temperature control purposes, signals from the temperature sensors are transmitted to the source of coagulation energy by way of wires 42 (FIG. 4) that are also connected to the aforementioned PC board 38 in the catheter handle. Suitable temperature sensors and controllers which control power to electrodes based on a sensed temperature are disclosed in U.S. Pat. Nos. 5,456,682, 5,582,609 and 5,755,715.

The temperature sensors are also preferably located within a linear channel (not shown) that is formed in the distal member. The linear channel insures that the temperature sensors will directly face the tissue and be arranged in linear fashion. The illustrated arrangement results in more accurate temperature readings which, in turn, results in better temperature control. As such, the actual tissue temperature will more accurately correspond to the temperature set by the physician on the power control device, thereby providing the physician with better control of the lesion creation process and reducing the likelihood that embolic materials will be formed. Such a channel may be employed in conjunction with any of the electrode (or other operative element) supporting structures disclosed herein.

Finally, the electrodes 20 and temperature sensors 128 can include a porous material coating, which transmits coagulation energy through an electrified ionic medium. For example, as disclosed in U.S. Pat. No. 5,991,650, electrodes and temperature sensors may be coated with regenerated cellulose, hydrogel or plastic having electrically conductive components. With respect to regenerated cellulose and other micro-porous materials, the coating acts as a mechanical barrier between the surgical device components, such as electrodes, preventing ingress of blood cells, infectious agents, such as viruses and bacteria, and large biological molecules such as proteins, while providing electrical contact to the human body. The micro-porous material coating also acts as a biocompatible barrier between the device components and the human body, whereby the components can now be made from materials that are somewhat toxic (such as silver or copper).

V. Operative Element Identification

Certain power source and control devices, such as the Cobra® electrosurgical unit manufactured by EP Technologies, Inc., allow the physician to individually select which of the electrodes 20 will be supplied with power. In a seven electrode arrangement, for example, the power supply and control device will include seven on-off switches that respectively correspond to the seven electrodes 20. Such an arrangement allows the physician to selectively enable only those electrodes that, for example, are located outside the outer member 22 after a loop has been formed around an anatomical structure. Nevertheless, it can be difficult for the physician to accurately determine how many of the electrodes are outside the outer member 22 during a surgical procedure where the physician makes use of a direct line of sight into the patient because some of the electrodes may be located behind the anatomical structure.

Figure 18:
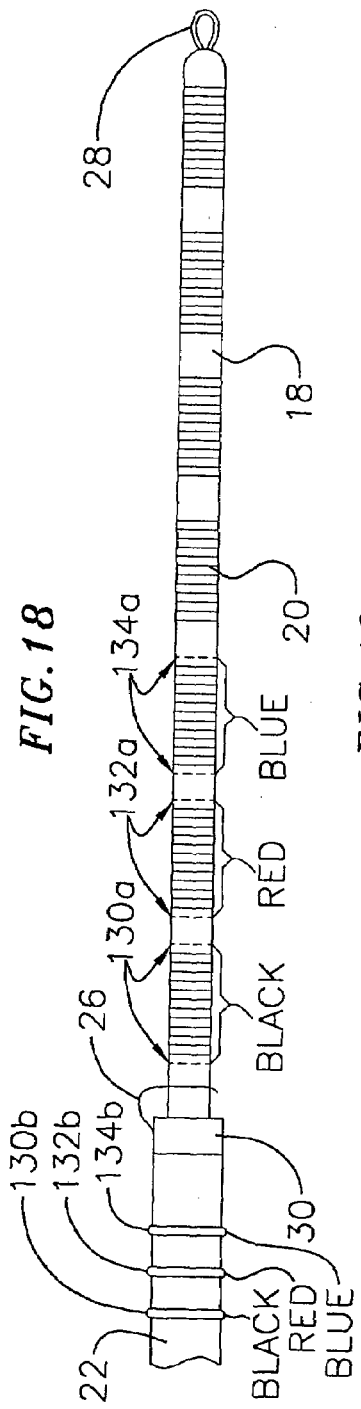
FIG. 18 is a plan view showing a portion of a surgical device and electrode identification system in accordance with a preferred embodiment of a present invention.

An electrode identification system in accordance with a present invention may be provided to enable the physician to readily determine how many of the electrodes are located outside of an outer member. The identification system, one embodiment of which is illustrated in FIG. 18, includes indicia associated with the electrodes and corresponding indicia on the outer member. More specifically, the illustrated embodiment includes unique indicia (i.e. the indicia that are visually distinguishable from one another) 130*a*, 132*a* and 134*a* on the distal member 18, each of which corresponds to a particular one of the proximal-most three of the seven electrodes 20, and corresponding indicia 130*b*, 132*b* and 134*b* on the distal portion of the outer member 22. The exemplary indicia is in the form of colored rings or bands. Indicia 130*a* and 130*b* are black, indicia 132*a* and 132*b* are red, and indicia 134*a* and 134*b* are blue. The order of the indicia (i.e. black, red, blue) is the same on the distal member 18 and outer member 22.

The indicia is used by the physician in the following manner. When a loop is formed around pulmonary veins in the manner illustrated in FIG. 5, a number of electrodes 20 will be located behind the pulmonary veins (from the physicians perspective) and one of the electrodes will be located immediately adjacent the distal end of the outer member 22. If, for example, the indicia associated with the electrode 20 adjacent the distal end of the outer member 22 is the blue indicia 134*a*, the physician will know by reviewing the indicia on the distal end of the outer member that there are two electrodes proximal to the "blue" electrode (i.e. the electrode associated with the red indicia 132*b* and the electrode associated with the black indicia 130*b*). Given the fact that two of the electrodes 20 are located within the outer member 22, the physician will be able to determine that the distal-most five electrodes are in contact with tissue, despite the fact that one or more of the five electrodes is not visible by direct observation because they are behind the pulmonary veins.

The number of electrodes that have indicia associated therewith, as well as the percentage of the total number electrodes that have indicia associated therewith, will depend on the particular surgical procedure for which the identification system is intended. Other visible indicia, such as alpha-numeric symbols or shading, may also be employed. Additionally, although the embodiment of the system illustrated in FIG. 18 is shown in combination with the surgical device illustrated in FIGS. 1A and 1B, other devices, such as those disclosed in the present specification, may also be provided with such a system.

VI. Masking

The portion of an operative element that is not intended to contact tissue (or be exposed to the blood pool) may be masked through a variety of techniques with a material that is preferably electrically and thermally insulating. This prevents the transmission of coagulation energy directly into the blood pool and directs the energy directly toward and into the tissue. This also prevents collateral damage to tissue by blocking transmission of coagulation energy into adjacent, non-target tissue. In the context of epicardial lesion creation, such non-target tissue may include the phrenic nerve and lung tissue.

For example, a layer of UV adhesive (or another adhesive) may be painted on preselected portions of the electrodes to insulate the portions of the electrodes not intended to contact tissue. Deposition techniques may also be implemented to position a conductive surface only on those portions of the assembly intended to contact tissue. A coating may also be formed by dipping the electrodes in PTFE material.

Figure 19:
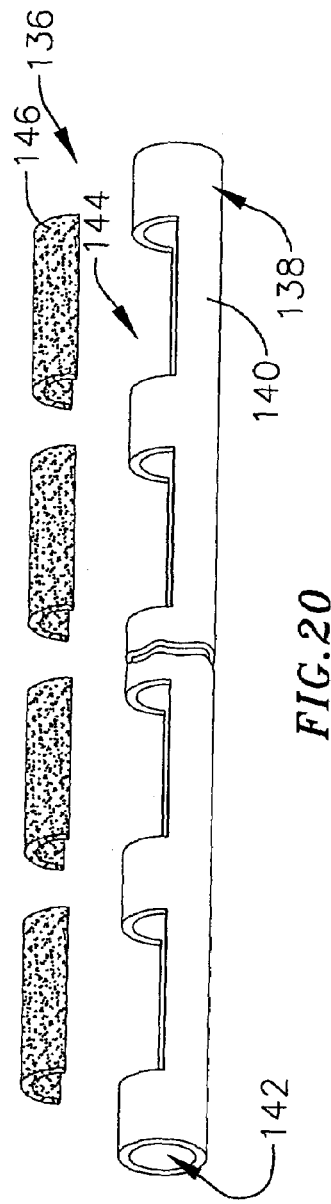
FIG. 19 is an exploded perspective view of a mask element in accordance with a preferred embodiment of a present invention.

Alternatively, a mask element may be positioned over a structure that supports one or more electrodes or other operative element to electrically and thermally insulate the desired portions thereof. As illustrated for example in FIGS. 19 and 20, a mask element 136 in accordance with one embodiment of a present invention includes a main body 138, having a side wall 140 defining an interior bore 142 and a plurality of openings 144, and a plurality of fluid retention elements 146 located in the openings. The main body 138 is preferably formed from material that is electrically and thermally insulating. The fluid retention elements 146 may be used to retain a conductive liquid such as saline and release the liquid during diagnostic or therapeutic procedures. When, for example, the mask element 136 is placed over the exemplary distal member 18, coagulation energy from the electrodes 20 will only be transmitted through the openings 144.

With respect to materials, the main body 138 is preferably formed from an elastic material that will hold the mask element 136 on the distal member 18 or other operative element supporting structure, yet also allow the surgeon to rotate the main body to focus the coagulation energy, or remove the mask element altogether, as desired. A suitable elastic material is silicone rubber having a thickness that ranges from about 0.05 mm to about 1 mm, depending on the desired level of insulation. For some surgical devices, the main body 138 need only be bendable, as opposed to elastic. Here, biocompatible plastics that are commonly used in catheters, such as Pebax® material and polyurethane, may be employed and the main body 138 secured to the surgical device with an adhesive.

Suitable materials for the fluid retention elements 146 include biocompatible fabrics commonly used for vascular patches (such as woven Dacron®), open cell foam materials, hydrogels, macroporous balloon materials (with very slow fluid delivery to the surface), and hydrophilic microporous materials. The effective electrical resistivity of the fluid retention elements 146 when wetted with 0.9% saline (normal saline) should range from about 1 $\Omega$-cm to about 2000 $\Omega$-cm.

Because it is important that the physician be able to identify the electrodes 20 or other operative elements that are in contact with tissue, the exemplary main body 138 should either be transparent or be provided with indicia (not shown) that allows the physician to distinguish between the electrodes. Such indicia, which may be printed directly onto the main body 138 with biocompatible ink, includes color coding, alpha-numeric indicia and shading.

Figure 20:
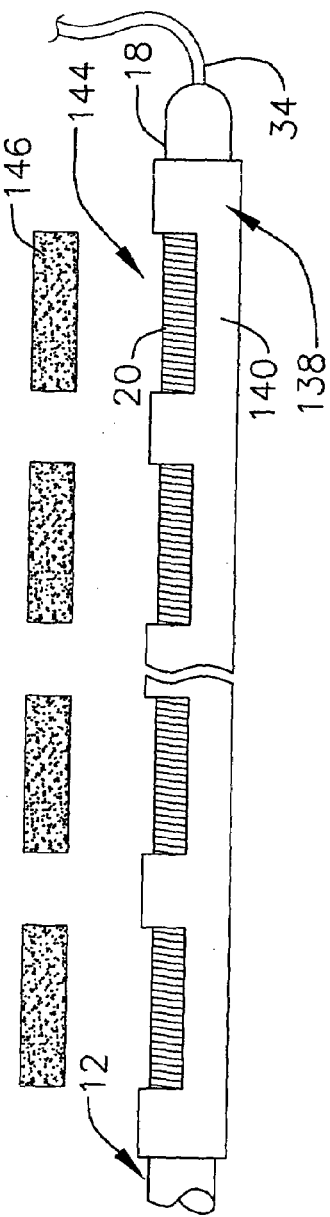
FIG. 20 is an exploded side view of the mask element illustrated in FIG. 19 in combination with a surgical device that carries a plurality of electrodes.

Mask elements in accordance with the present invention may be used in conjunction with devices other that the shaft and spaced closed coil electrode structure illustrated in FIG. 20. For example, the closed coil electrodes may be replaced with open coil electrodes or a straight piece of wire. Also, temperature sensors may be moved from the underlying support structure to a portion of the mask element, preferably to the fluid retention elements. The temperature sensors could be woven into fabric fluid retention material or embedded in fluid retention elements formed from other materials. Here, however, rotational movement of the mask element should be limited to, for example, 180 degrees in order to prevent damage to the signal wires that will be connected to the temperature sensors.

VII. Clamp Devices

As illustrated for example in FIGS. 21–24, a clamp device 148 in accordance with a preferred embodiment of a present invention includes a forceps-like apparatus 150 and a tissue coagulation apparatus 152. The forceps-like apparatus 150 includes arms 154 and 156 that are pivotably secured to one another by a pin 158 to allow the device to be opened and closed. The proximal portions of the arms 154 and 156 may be formed from rigid or malleable material. The arm distal portions 160 and 162, which are curved and support the tissue coagulation apparatus 152, are preferably formed from malleable material. This allows the arm distal portions 160 and 162 to be re-shaped by the physician as needed for particular procedures and body structures (note the dash lines in FIG. 21). Alternatively, one or both of the arm distal portions 160 and 162 may be formed from rigid material. The arm distal portions 160 and 162 and, preferably the entire forceps-like apparatus 150, will be coated with a layer of insulating material (not shown), such as heat shrink Pebax® material, polyester, or polyurethane. A pair of handles 164 and 166 are mounted on the proximal ends of the arms 154 and 156.

The exemplary tissue coagulation apparatus 152 includes an operative element support member 168 that may be formed from a soft, flexible, insulative, biocompatible thermoplastic material such as Pebax® material, polyethylene, or polyurethane. In the illustrated embodiment, which may be used to form lesions around one or more pulmonary veins, the operative element support member 168 will preferably be about 5 French to about 9 French in diameter.

Referring more specifically to FIG. 21, the operative element support member 168 is a continuous structure, but for the break at the distal end of the arm distal portions 160 and 162 that allows the device to be opened and closed, which will form a continuous loop around a body structure when the clamp device is in the closed position illustrated in FIG. 21. As such, the electrodes 20 (or other operative element) supported thereon may be used to create a continuous lesion pattern in tissue when coagulation energy is applied simultaneously to the electrodes. Additionally, the curvature of the arm distal portions 160 and 162 and operative element support member 168 allow the physician to apply pressure to a body structure, such as a pulmonary vein, that is adequate to enable the formation of a single continuous transmural lesion all the way around the body structure in one step without collapsing the body structure, as would be the case with a device having straight arm distal portions. The open region defined by the arm distal portions 160 and 162 and operative element support member 168 may be substantially circular, oval or any other closed shaped necessary for a particular procedure.

The operative element support member 168 is preferably mounted off center by an angle θ on the arm distal portions 160 and 162, as best seen in FIG. 24. In the illustrated embodiment, the operative element support member 168 is approximately 45 degrees off center. Such positioning provides a number of advantages. For example, the off center positioning focuses the coagulation energy downwardly (towards the heart) and inwardly (towards the pulmonary veins) when the tissue coagulation apparatus 152 is positioned around one or more pulmonary veins. So positioned, with side A advanced against heart tissue, the insulated arm distal portions 160 and 162 act as a shield to prevent the coagulation of tissue other than that targeted for coagulation. Moreover, the physicians view of the tissue in contact with the tissue coagulation apparatus 152 will not be blocked by the arm distal portions 160 and 162.

As illustrated for example in FIGS. 21–23, an electrical conduit 170 connects the tissue coagulation apparatus 152 to an electrical connector 172 that may be connected to a source of RF coagulation energy. More specifically, signal wires 41 and 42 from the electrodes and temperature sensors on the tissue coagulation apparatus 152 run through the electrical conduit 170 along the arm 156 to the electrical connector 172.

Figure 25:
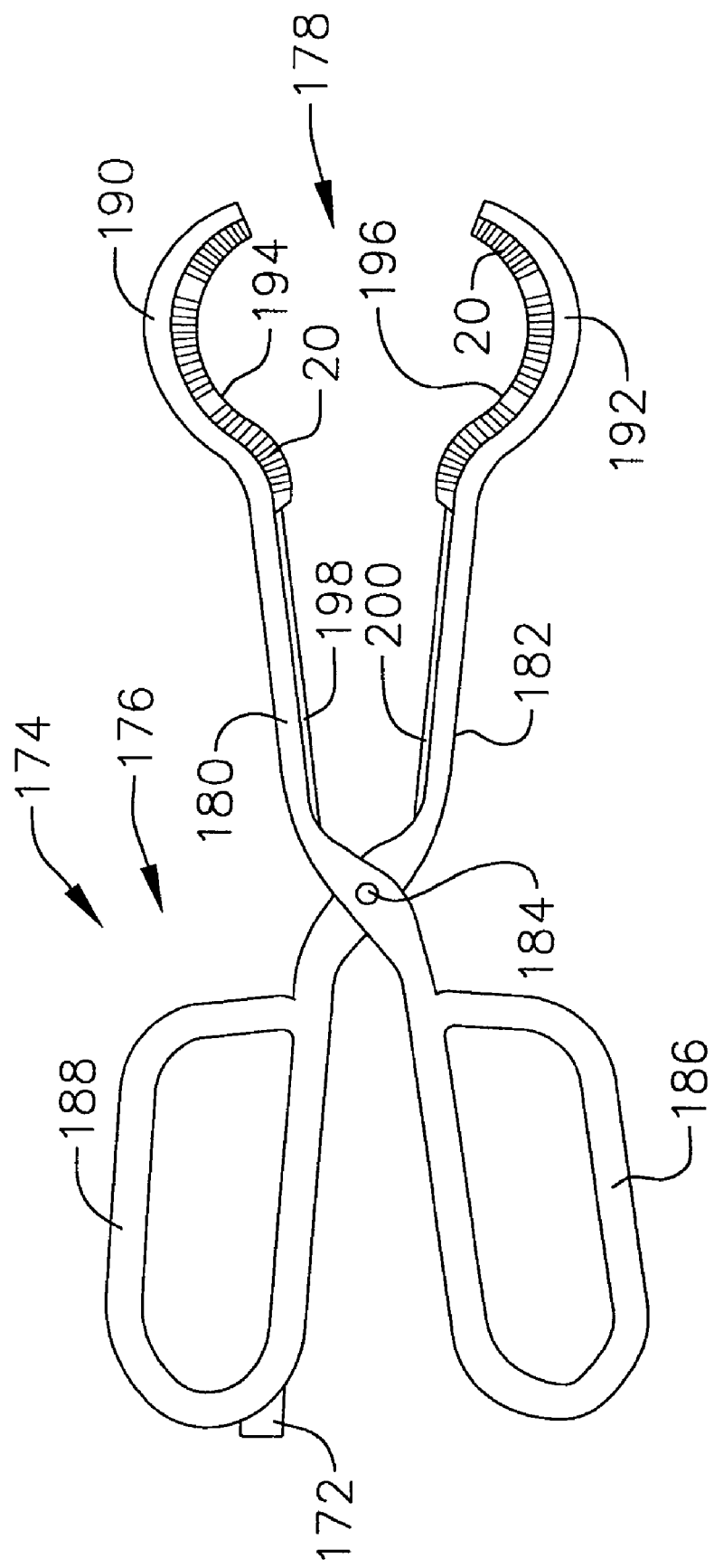
FIG. 25 is a plan view of a clamp device in accordance with a preferred embodiment of a present invention.

Another exemplary clamp device, which is generally represented by reference numeral 174, is illustrated in FIG. 25. Like the exemplary clamp device illustrated in FIGS. 21–24, clamp device 174 includes a forceps-like device 176 and a tissue coagulation apparatus 178 which, unless otherwise indicated, are essentially the same as the forceps-like device and tissue coagulation apparatus illustrated in FIGS. 21–24. Here, however, the proximal ends of the arms 180 and 182 are pivotably secured to one another by a pin 184 and the handles 186 and 188 are located just proximally of the pin. Also, given the distance that the curved arm distal portions 190 and 192 are capable of moving from one another, the tissue coagulation apparatus 178 includes a pair of operative element support members 194 and 196 that are connected to the connector 172 by a pair of electrical conduits 198 and 200.

It should also be noted that the although the exemplary clamp devices illustrated above employ a forceps-like apparatus having a pair of arms connected by a pivot pin to position the tissue coagulation apparatus around tissue, other apparatus may also be employed. For example, an elongate apparatus including a scissors-like handle at one end, curved distal portions at the other end, and a suitable mechanical linkage joining the two may be employed.

VIII. Methods

In accordance with an invention herein, surgical devices such as those describe above may be used to support an operative element on the outer surfaces of body structures for diagnostic and/or therapeutic purposes. In the context of the treatment of atrial fibrillation, for example, surgical devices with loop structures such as those described above may be used to support an operative element, such as a plurality of spaced electrodes, that creates transmural epicardial lesions to isolate the sources of focal (or ectopic) atrial fibrillation.

Turning to FIG. 26, an exemplary method of treating focal atrial fibrillation with a device such as that illustrated in FIG. 5 involves the creation of transmural lesions around the pulmonary veins. Lesions may be created around the pulmonary veins individually or, as is illustrated in FIG. 26, a first transmural epicardial lesion 202 may be created around the right pulmonary vein pair RPV and a second transmural epicardial lesion 204 may be created around the left pulmonary vein pair LPV. Thereafter, if needed, a linear transmural epicardial lesion 206 may be created between the right and left pulmonary vein pairs RPV and LPV. A linear transmural lesion (not shown) that extends from the epicardial lesion 204 to the left atrial appendage may also be formed. The linear lesions may be formed with the probe described above with reference to FIGS. 17A and 17C. Other suitable surgical devices for creating linear lesions, one example of which would be the device illustrated in FIGS. 14–16 without the pull wire, are disclosed in aforementioned U.S. application Ser. No. 09/072,872.

Alternatively, as illustrated in FIG. 27, a single lesion 208 may be formed around all four of the pulmonary vein pairs RPV and LPV.

Access to the heart may be obtained via a thoracotomy, thoracostomy or median sternotomy. Ports may also be provided for cameras and other instruments.

Surgical devices with loop structures such as those described above may also be used to create transmural epicardial lesions in a maze pattern that controls electrical propagation within the left and right atria. More specifically, a maze pattern may be created by positioning a plurality of spaced electrodes, or other operative element, within the pericardial space around the exterior of the heart at the various locations needed to form the desired lesion pattern.

The surgical devices described above may also be urged through tissue planes (i.e. the space between fascia material and a particular organ) to properly position the device prior to the actuation of the operative elements. Such a procedure is referred to as blunt dissection.

The clamp devices illustrated in FIGS. 21–25 may also be used to form lesions such as pulmonary vein lesions 202, 204 and 208, or lesions around other body structures.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

We claim:

1. A surgical device, comprising:
    a shaft defining a distal region and a proximal end;
    a handle associated with the proximal end of the shaft; and
    an electrode, carried by the distal region of the shaft, defining a distal region and a pair of exterior openings in the distal region of the electrode, and located distally of the distal end of the shaft, connected by a through hole extending through the electrode, the through hole being closed but for the exterior openings in the distal region of the electrode.

2. A surgical device as claimed in claim 1, wherein the distal region of the shaft defines a distal end and the electrode comprises a tip electrode.

3. A surgical device as claimed in claim 2, further comprising:
    a plurality of spaced electrodes carried by the distal region of the shaft proximal to the tip electrode.

4. An electrode for use with a surgical device, comprising:
    a main body portion defining a distal region, a proximal region and a longitudinal axis;
    a pair of exterior openings formed in the distal region of main body portion without any structural member therein and connected by a through hole extending through the main body portion, the through hole being closed but for the exterior openings in the distal region and at least a portion of the through hole being oriented at a non-parallel angle to the longitudinal axis of the main body portion; and
    means, associated with the proximal region, for mounting the main body portion on the distal end of a hollow cylindrical shaft.

5. An electrode as claimed in claim 4, wherein the through hole is substantially perpendicular to the longitudinal axis.

6. An electrode as claimed in claim 4, wherein the through hole is substantially linear from one exterior opening to the other.

7. An electrode for use with a surgical device, comprising:
    a main body portion defining a distal region; and
    a pair of exterior openings formed in the distal region of main body portion without any structural member therein and connected by a through hole extending through the main body portion, the through hole being closed but for the exterior openings in the distal region and substantially v-shaped.

8. An electrode for use with a surgical device, comprising:
    a main body portion defining a distal region, a proximal region, a longitudinal axis and an interior lumen extending along at least a portion the longitudinal axis; and
    a pair of exterior openings formed in the distal region of main body portion without any structural member therein and connected by a through hole extending through the main body portion, the through hole being closed but for the exterior openings in the distal region and at least a portion of the through hole being oriented at a non-parallel angle to the longitudinal axis of the main body portion.

9. An electrode as claimed in claim 8 further comprising:
    a base member associated with the proximal region of the main body portion.

10. An electrode as claimed in claim 9, wherein the main body portion and the base member define respective perimeters measured about the longitudinal axis, and the perimeter of the base member is smaller than the perimeter of the main body portion.

11. An electrode as claimed in claim 9, wherein the base member defines an interior lumen that extends to the interior lumen of the main body portion.

* * * * *